(12) United States Patent
Sharp et al.

(10) Patent No.: US 9,279,124 B2
(45) Date of Patent: Mar. 8, 2016

(54) FIDGETIN-LIKE 2 AS A TARGET TO ENHANCE WOUND HEALING

(71) Applicant: ALBERT EINSTEIN COLLEGE OF MEDICINE OF YESHIVA UNIVERSITY, Bronx, NY (US)

(72) Inventors: David J. Sharp, Scarsdale, NY (US); Rabab Charafeddine, Bronx, NY (US)

(73) Assignee: Albert Einstein College of Medicine, Inc., Bronx, NY (US)

( * ) Notice: Subject to any disclaimer, the term of this patent is extended or adjusted under 35 U.S.C. 154(b) by 0 days.

(21) Appl. No.: 14/487,221

(22) Filed: Sep. 16, 2014

(65) Prior Publication Data
US 2015/0105447 A1   Apr. 16, 2015

Related U.S. Application Data

(63) Continuation of application No. 13/553,155, filed on Jul. 19, 2012, now Pat. No. 8,853,181.

(60) Provisional application No. 61/510,172, filed on Jul. 21, 2011.

(51) Int. Cl.
| | |
|---|---|
| *C12N 15/113* | (2010.01) |
| *A61K 31/713* | (2006.01) |
| *A61K 31/7105* | (2006.01) |
| *A61K 9/00* | (2006.01) |
| *A61K 9/06* | (2006.01) |
| *A61K 9/127* | (2006.01) |

(52) U.S. Cl.
CPC ............ *C12N 15/113* (2013.01); *A61K 9/0014* (2013.01); *A61K 9/06* (2013.01); *A61K 9/127* (2013.01); *A61K 31/713* (2013.01); *A61K 31/7105* (2013.01); *C12N 2310/14* (2013.01)

(58) Field of Classification Search
USPC ................. 435/6.1, 91.1, 91.31, 455; 514/44; 536/23.1, 24.5
See application file for complete search history.

(56) References Cited

U.S. PATENT DOCUMENTS

2009/0004668 A1   1/2009  Chen et al.

FOREIGN PATENT DOCUMENTS

WO          0244321        6/2002

OTHER PUBLICATIONS

Mukherjee S et al., entitled "Human Fidgetin is a Microtubule Severing the Enzyme and Minus-End Depolymerase that Regulates Mitosis," Cell Cycle, Jun. 15, 2012; 11(12):2359. Epub Jun. 15, 2012 (Abstract).
Yang Y et al., entitled "Functional Characterization of Fidgetin, an AAA-Family Protein Mutated in Fidget Mice," Exp. Cell Res. Mar. 10, 2005; 304(1):50. Epub Dec. 10, 2004 (Abstract).
Mukherjee S et al., entitled "Mammalian Fidgetin Proteins in Cell Migration and Morphogenesis," Mol. Cell. Biol. 21:126/B202, Meetings Abstract (Dec. 11, 2010).
Crooke S A, Rev Medicine, vol. 55, pp. 61-95 (2004).
Peracchi et al., Rev. Med. Virol., vol. 14, pp. 47-54 (2004).
Agrawal et al., Molecular Med. Today, vol. 6, pp. 72-81 (2000).
Chirila et al., Biomaterials, vol. 23, pp. 321-342 (2002).
Doench et al., Genes and Development, vol. 17, pp. 438-443 (2003).
Holen et al., Nucleic Acids Res., vol. 30, No. 8, pp. 1757-1766 (2002).
Opalinska et al., Nature Rev., vol. 1, pp. 503-514 (2002).

*Primary Examiner* — Jane Zara
(74) *Attorney, Agent, or Firm* — Amster, Rothstein & Ebenstein LLP

(57) ABSTRACT

Methods of treating a wound in a subject are provided comprising administering to the subject an amount of an inhibitor of Fidgetin-like 2. Compositions and pharmaceutical compositions comprising an amount of an inhibitor of Fidgetin-like 2 are also provided. Methods are also provided for identifying an inhibitor of Fidgetin-like 2.

2 Claims, 13 Drawing Sheets

FIDGETIN-LIKE 2 AS A TARGET TO ENHANCE WOUND HEALING

CROSS-REFERENCE TO RELATED APPLICATIONS

This application is a continuation of U.S. patent application Ser. No. 13/553,155, filed Jul. 19, 2012, now allowed, which claims the benefit of U.S. Provisional Patent Application No. 61/510,172, filed Jul. 21, 2011, the contents of each of which are herein incorporated by reference in their entirety.

STATEMENT OF GOVERNMENT SUPPORT

This invention was made with government support under grant number GM065940 awarded by the National Institute of General Medical Sciences. The government has certain rights in the invention.

SEQUENCE LISTING INCOPORATION

The ".txt" Sequence Listing filed with this application by EFS and which is entitled 96700_1855_ST25.txt, is 26 kilobytes in size and which was created on Jun. 11, 2012, is hereby incorporated by reference.

BACKGROUND OF THE INVENTION

The disclosures of all publications, patents, patent application publications and books referred to in this application are hereby incorporated by reference in their entirety into the subject application to more fully describe the art to which the subject invention pertains.

The development of safe and effective therapies for treating acute and chronic wounds is an issue currently of great interest to clinical scientists and industry, alike. Wound healing is an intricate, multi-stage process that relies heavily on the delivery of new cells to the wound zone. Two key elements of the wound healing response are fibroplasia and epithelialization when fibroblasts and epithelial cells, respectively, enter the wound to form a protective barrier from the external environment. This is stimulated by cell proliferation and migration from the wound edge. The identification of agents that increase the rate at which cells invade and close a wound would represent a major advance in wound healing therapeutics. Ideally, this would be a topically applied agent that stimulates the proliferation and migration of fibroblasts and wound edge epithelial cells.

The present invention addresses this need and identifies a novel target in promoting wound healing and provides therapies and assays based thereon.

SUMMARY OF THE INVENTION

A method of treating a wound in a subject is provided comprising administering to the subject an amount of an inhibitor of Fidgetin-like 2 effective to treat the wound.

A pharmaceutical composition is provided comprising an amount of an inhibitor of Fidgetin-like 2.

A method for identifying a candidate agent for treating a wound comprising:
a) determining the activity of an amount of Fidgetin-like 2; and
b) contacting the amount of Fidgetin-like 2 with the candidate agent and determining the activity of the amount of Fidgetin-like 2 in the presence of the candidate agent, wherein a decreased activity of the amount of Fidgetin-like 2 in the presence of the candidate agent as compared to the activity of Fidgetin-like 2 in the absence of the candidate agent indicates that the candidate agent can treat a wound, and wherein no change in or an increased activity of the amount of Fidgetin-like 2 in the presence of the candidate agent as compared to the activity of Fidgetin-like 2 in the absence of the candidate agent does not indicate that the candidate agent can treat a wound.

An inhibitor of Fidgetin-like 2 is provided for treating a wound or promoting wound healing.

BRIEF DESCRIPTION OF THE DRAWINGS

FIG. 1A shows a Western blot of human U2OS cell lysates probed with an anti-Fidgetin-like 2 antibody generated in-lab. This antibody recognizes a single band that is substantially decreased by Fidgetin-like 2 siRNA treatment (see FIG. 2 below). FIG. 1B shows a migrating U2OS cell double-labeled for Fidgetin-like 2 and microtubules. At high magnification (inset), Fidgetin-like 2 clearly co-localizes with spans of the microtubule lattice near the cell edge.

FIG. 2A shows Western blots of U2OS cell lysates obtained from control (N) and Fidgetin-like 2 siRNA treated cultures (72 hrs. after treatment). Actin was used as a loading control. FIG. 2B shows time-lapse phase contrast images of "wound healing" assays performed in control and Fidgetin-like 2 siRNA treated cultures. In these assays, a monolayer of U2OS cells is "wounded" by a pipette tip and the invasion of cells into the wound is monitored over time. FIG. 2C shows the average rate of wound closure in each condition which is increased nearly 4-fold after Fidgetin-like 2 siRNA. FIG. 2D shows the trajectories of single control and Fidgetin-like 2 siRNA treated cells as they enter the wound zone. Not only do Fidgetin-like 2 siRNA-treated cells move several-fold faster than controls, they also display more directionally persistent migration as indicated in FIG. 2E.

DETAILED DESCRIPTION OF THE INVENTION

Figures 1A, 1B:
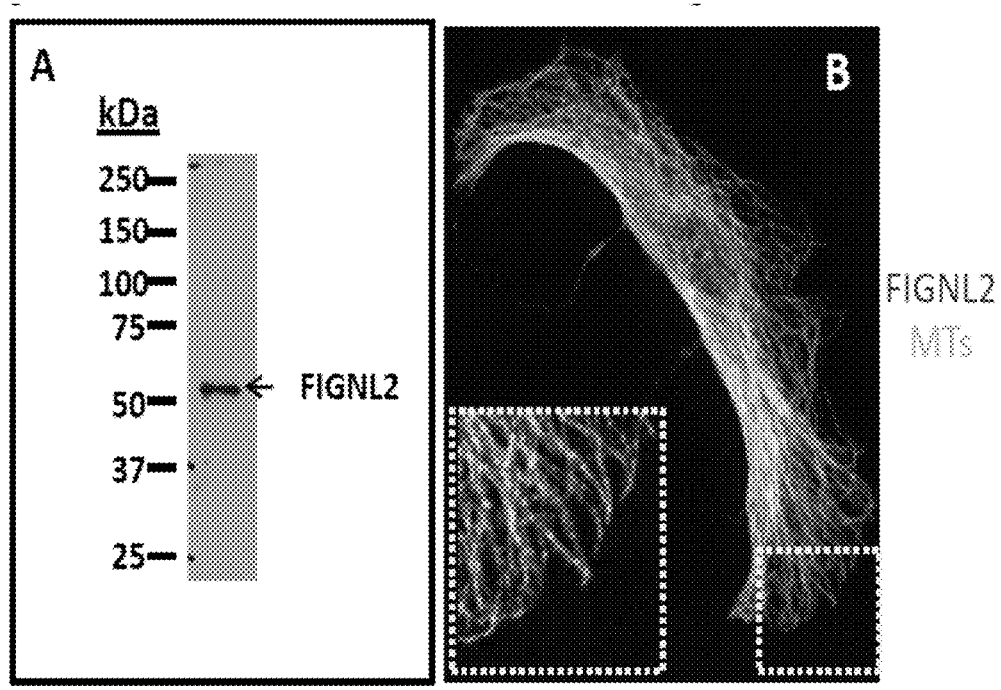
FIG. 1A-1B: Fidgetin-like 2 is expressed in human tissue culture cells where it localizes to microtubules.

A method of treating a wound in a subject is provided comprising administering to the subject an amount of an inhibitor of Fidgetin-like 2 effective to treat a wound.

In an embodiment, the amount of inhibitor of Fidgetin-like 2 is effective to accelerate wound healing.

In an embodiment, the inhibitor of Fidgetin-like 2 is administered locally to the wound. In an embodiment, the inhibitor of Fidgetin-like 2 is administered via a vein or artery. In an embodiment, the inhibitor of Fidgetin-like 2 is administered by injection, catheterization or cannulation. In an embodiment, the inhibitor of Fidgetin-like 2 is administered from an implant that elutes the inhibitor, for example a eluting stent or an eluting skin patch.

In an embodiment, the inhibitor of Fidgetin-like 2 is administered topically to the wound.

In an embodiment, the inhibitor of Fidgetin-like 2 is a nucleic acid. In an embodiment, the inhibitor of Fidgetin-like 2 is an siRNA or shRNA. In an embodiment, the nucleic acid is directed against a DNA encoding Fidgetin-like 2 or against an mRNA encoding Fidgetin-like 2.

In an embodiment of the method, the inhibitor of Fidgetin-like 2 is encapsulated in a nanoparticle. In an embodiment the nanoparticle is a liposomal nanoparticle.

In an embodiment, the Fidgetin-like 2 is human Fidgetin-like 2.

In an embodiment, the Fidgetin-like 2 comprises consecutive amino acid residues having the sequence set forth in SEQ ID NO:2.

In an embodiment, the wound is an epidermal wound. In an embodiment, the wound is a skin wound.

In an embodiment, the wound is a cardiac tissue wound. In an embodiment, the wound is a cardiovascular wound, for example resulting from a myocardial infarction.

In an embodiment, the wound is a neuronal wound.

A pharmaceutical composition is provided comprising an amount of an inhibitor of Fidgetin-like 2. In an embodiment, the pharmaceutical composition comprises an amount of an inhibitor of Fidgetin-like 2 effective to treat a wound in a human subject. In an embodiment, the wound is a skin wound. In an embodiment, the wound is an epidermal wound.

In an embodiment, the pharmaceutical composition comprises a pharmaceutically acceptable carrier.

In an embodiment of the pharmaceutical composition the inhibitor of Fidgetin-like 2 is a nucleic acid.

In an embodiment of the pharmaceutical composition the inhibitor of Fidgetin-like 2 is an siRNA or shRNA.

In an embodiment of the pharmaceutical composition the nucleic acid is directed against a DNA encoding Fidgetin-like 2 or against an mRNA encoding Fidgetin-like 2.

In an embodiment of the pharmaceutical composition, the inhibitor of Fidgetin-like 2 is encapsulated in a nanoparticle. In an embodiment the nanoparticle is a liposomal nanoparticle.

In an embodiment of the pharmaceutical composition the Fidgetin-like 2 is human Fidgetin-like 2.

In an embodiment of the pharmaceutical composition the Fidgetin-like 2 comprises SEQ ID NO:2.

A method for identifying a candidate agent for treating a wound comprising:
a) determining the activity of an amount of Fidgetin-like 2; and
b) contacting the amount of Fidgetin-like 2 with the candidate agent and determining the activity of the amount of Fidgetin-like 2 in the presence of the candidate agent, wherein a decreased activity of the amount of Fidgetin-like 2 in the presence of the candidate agent as compared to the activity of Fidgetin-like 2 in the absence of the candidate agent indicates that the candidate agent can treat a wound, and wherein no change in or an increased activity of the amount of Fidgetin-like 2 in the presence of the candidate agent as compared to the activity of Fidgetin-like 2 in the absence of the candidate agent does not indicate that the candidate agent can treat a wound.

In an embodiment, the Fidgetin-like 2 is human Fidgetin-like 2.

In an embodiment, the Fidgetin-like 2 comprises SEQ ID NO:2.

In an embodiment, the candidate agent is a small molecule of 2000 Daltons or less. In an embodiment, the candidate agent is a small molecule of 1000 Daltons or less. In an embodiment, the candidate agent is a substituted or un-substituted hydrocarbon small molecule.

An inhibitor of Fidgetin-like 2 is provided for treating a wound or promoting wound healing.

In an embodiment, the inhibitor of Fidgetin-like 2 is a nucleic acid.

In an embodiment, the inhibitor is an siRNA or shRNA.

In an embodiment, the nucleic acid is directed against a DNA encoding Fidgetin-like 2 or against an mRNA encoding Fidgetin-like 2.

In an embodiment, the Fidgetin-like 2 is human Fidgetin-like 2.

In an embodiment, the Fidgetin-like 2 comprises SEQ ID NO:2.

In an embodiment, the inhibitor or the candidate agent is an aptamer, a nucleic acid, an oligonucleotide, or a small organic molecule of 2000 Daltons or less. In an embodiment, the inhibitor is cell-membrane permeable.

The dosage of the inhibitor administered in treatment will vary depending upon factors such as the pharmacodynamic characteristics of a specific inhibitor and its mode and route of administration; the age, sex, metabolic rate, absorptive efficiency, health and weight of the recipient; the nature and extent of the symptoms; the kind of concurrent treatment being administered; the frequency of treatment with the inhibitor and the desired therapeutic effect.

A dosage unit of the inhibitor may comprise a single compound, or a mixture of the compound with one or more anti-infection compound(s) or wound healing-promoting compound(s).

In an embodiment, the siRNA (small interfering RNA) as used in the methods or compositions described herein comprises a portion which is complementary to an mRNA sequence encoding a Fidgetin-like 2 protein. In an embodiment, the Fidgetin-like 2 protein is a human Fidgetin-like 2 protein. In an embodiment, the mRNA is encoded by the DNA sequence NCBI Reference Sequence: NM_001013690.4 (SEQ ID NO:1), and the siRNA is effective to inhibit expression of Fidgetin-like 2 protein. In an embodiment, the Fidgetin-like 2 protein comprises consecutive amino acid residues having the sequence set forth in SEQ ID NO:2.

In an embodiment, the siRNA comprises a double-stranded portion (duplex). In an embodiment, the siRNA is 20-25 nucleotides in length. In an embodiment the siRNA comprises a 19-21 core RNA duplex with a one or two nucleotide 3' overhang on, independently, either one or both strands. The siRNA can be 5' phosphorylated, or not, and may be modified with any of the known modifications in the art to improve efficacy and/or resistance to nuclease degradation. In an embodiment the siRNA can be administered such that it is transfected into one or more cells. In an embodiment, the siRNA is 5' phosphorylated.

In an embodiment, the 5' terminal residue of a strand of the siRNA is phosphorylated. In an embodiment the 5' terminal residue of the antisense strand of the siRNA is phosphorylated. In one embodiment, a siRNA of the invention comprises a double-stranded RNA wherein one strand of the double-stranded RNA is 80, 85, 90, 95 or 100% complementary to a portion of an RNA transcript of a gene encoding Fidgetin-like 2 protein. In an embodiment, the RNA transcript of a gene encoding Fidgetin-like 2 protein is an mRNA. In an embodiment, the Fidgetin-like 2 protein is a human Fidgetin-like 2 protein. In an embodiment, a siRNA of the invention comprises a double-stranded RNA wherein one strand of the RNA comprises a portion having a sequence the same as a portion of 18-25 consecutive nucleotides of an RNA transcript of a gene encoding Fidgetin-like 2 protein. In an embodiment, the Fidgetin-like 2 protein is a human Fidgetin-like 2 protein. In yet another embodiment, a siRNA of the invention comprises a double-stranded RNA wherein both strands of RNA are connected by a non-nucleotide linker. Alternately, a siRNA of the invention comprises a double-stranded RNA wherein both strands of RNA are connected by a nucleotide linker, such as a loop or stem loop structure.

In one embodiment, a single strand component of a siRNA of the invention is from 14 to 50 nucleotides in length. In another embodiment, a single strand component of a siRNA of the invention is 14, 15, 16, 17, 18, 19, 20, 21, 22, 23, 24, 25, 26, 27, or 28 nucleotides in length. In yet another embodiment, a single strand component of a siRNA of the invention is 21 nucleotides in length. In yet another embodiment, a single strand component of a siRNA of the invention is 22 nucleotides in length. In yet another embodiment, a single strand component of a siRNA of the invention is 23 nucleotides in length. In one embodiment, a siRNA of the invention is from 28 to 56 nucleotides in length. In another embodiment, a siRNA of the invention is 40, 41, 42, 43, 44, 45, 46, 47, 48, 49, 50, 51, or 52 nucleotides in length.

In another embodiment, an siRNA of the invention comprises at least one 2'-sugar modification. In another embodiment, an siRNA of the invention comprises at least one nucleic acid base modification. In another embodiment, an siRNA of the invention comprises at least one phosphate backbone modification. As used herein, "at least one" means one or more.

In one embodiment, RNAi inhibition of Fidgetin-like 2 protein is effected by a short hairpin RNA ("shRNA"). The shRNA is introduced into the appropriate cell by transduction with a vector. In an embodiment, the vector is a lentiviral vector. In an embodiment, the vector comprises a promoter. In an embodiment, the promoter is a U6 or H1 promoter. In an embodiment the shRNA encoded by the vector is a first nucleotide sequence ranging from 19-29 nucleotides complementary to the target gene/mRNA, in the present case the mRNA encodes Fidgetin-like 2 protein. In an embodiment the Fidgetin-like 2 protein is a human Fidgetin-like 2 protein. In an embodiment the shRNA encoded by the vector also comprises a short spacer of 4-15 nucleotides (a loop, which does not hybridize) and a 19-29 nucleotide sequence that is a reverse complement of the first nucleotide sequence. In an embodiment the siRNA resulting from intracellular processing of the shRNA has overhangs of 1 or 2 nucleotides. In an embodiment the siRNA resulting from intracellular processing of the shRNA overhangs has two 3' overhangs. In an embodiment the overhangs are UU.

```
NCBI Reference Sequence: NM_001013690.4
(nucleic acid encoding Human Fidgetin-like 2)
                                                     (SEQ ID NO: 1)
  1    agtgagctat gggacacta ctgcactgta gcctgggcaa cagagcaaga ccttgtctca 61    aaaatgtata tatattttgg gctttttttc ctaaaacggg aactacaaca gcatatttgc 121    gagctgatga gagtgaccca gcagagaggg aaatggatca gctctgttga agatgcactg 181    gacaccagaa cacgcccagc ccctcaacca gtggccagag cagcacctgg acgtctcctc
```

-continued

```
 241 caccacccecg tcgccggccc acaagttgga gttgcccect gggggtcgcc aacgctgcca
 301 ctacgcttgg gcacacgacg acatctcagc cctcactgcc tccaacctcc taaagcgcta
 361 tgcagagaag tactctgggg tcttggattc tccctacgag cgtccggccc tgggcgggta
 421 cagcgacgcc tccttcctca acggcgccaa aggggatccc gagccctggc cagggccgga
 481 gccaccctac cccttggcct cactccacga aggcctccca ggaaccaaat cgggcggtgg
 541 cggcggttcc ggggccctgg ggggctcccc agttttagcc gggaacctcc ctgaacccct
 601 ctacgccggc aatgcgtgcg ggggcccatc ggcggcgccc gagtacgcgg ccggctacgg
 661 cgggggggtac ctggcgccgg gttactgcgc gcagacgggc gccgcgctgc cccgccgcc
 721 cccggccgcg ctcctgcagc ccccaccgcc tccggggtac gggccctcag cgccgctgta
 781 caactatccc gcagggggct acgcagcgca gcccggctat ggcgcgctcc cgccgccccc
 841 aggcccaccc ccggccccct acctgacccc gggcctgccc gcgcccacgc ccctgcccgc
 901 gccggcaccg cccaccgcct atggcttccc cacgccgcg ccgggtgccg aatccgggct
 961 gtcgctgaag cgcaaggccg ccgacgaggg gcccgagggc cgctaccgca agtacgcgta
1021 cgagcccgcc aaggcccccg tggctgacgg agcctcctac cccgccgcgg acaacggcga
1081 atgtcggggc aacgggttcc gggccaagcc gccaggagcc gcggaggagg cgtcgggcaa
1141 gtacggtggc ggcgtcccec tcaaggtcct gggctccccc gtctacggcc gcaactgga
1201 gccctttgaa aagttcccgg agcgggcccc ggctcctcgt gggggttcg ccgtgccgtc
1261 gggggagact cccaaaggcg tggaccctgg ggccctggag ctggtgacga gcaagatggt
1321 ggactgcggg ccccggtgc agtgggcgga tgtggcgggc cagggcgcgc tcaaggcggc
1381 gctggaggag gagctggtgt ggcccctgct caggccgccc gcctacccgg gcagcctgcg
1441 cccgccgcgg accgtcctgc tctttgggcc gcggggcgcg ggcaaagcgc tgctgggccg
1501 ctgcctcgcc acgcagctgg gcgccacgct gttgcgcctg cgcggcgcga ccctggctgc
1561 gcccggcgcc gccgagggcg cgcgcctcct ccaggccgcc ttcgcggccg cgcgctgccg
1621 cccacccctcc gtactcctca tcagcgagct agaggcgctg ctccccgccc gggacgacgg
1681 cgcggcggca ggggcgcgc tgcaggtgcc gctcctggcc tgcctggacg ggggctgcgg
1741 cgcggggget gacggcgtgc tggttgtggg caccacctcg cggcccgcgg ctctggacga
1801 ggcgacccgc cggcgcttct ctctccgctt ctacgtggcg ctgcccgaca gcccggcccg
1861 cgggcagatc ctgcagcggg cgctggccca gcagggctgc gcgctcagtg agcgggaact
1921 ggcggcgctg gtgcagggca cgcagggctt ctctggggc gagctggggc agctgtgcca
1981 gcaggcggcg gccggggcgg gcctcccggg gctgcagcgc cccctctcct acaaggacct
2041 ggaggcgcg ctggccaagg tgggccctag ggcctctgcc aaggaactgg actcgttcgt
2101 ggagtgggac aaaatgtacg gctccggaca ctgacggcgc gcggggagg ccgcgggagc
2161 cgcagtccct ccgtcccogc cgcctccgcg tgggagggat gtcactgact aaacccggct
2221 ggcaggggct ggagtggtga atgtgggatc ggggacagga ggggtctgcc ggtggatatt
2281 ttttttttcg tgggaaggaa aatgcttctg ccaggcagat gccatatgcg ccgtgtactc
2341 aggtttttcc tatttattgt ggactggaag ctcgccatct ccgcccggca gaccgggcag
2401 atccggcatg ggctggcacc cggggcctta agaactcctg ctctcttgcc acaacgcttt
2461 tgtctcctcg ctatctgaat ggcaccctcc ttctccctca ctctctccat cccattctct
2521 gcattctctt ggttttctct ccctttgct ttgtcgctga caccectgcc cacccatgc
2581 tggccctgtt tctctcctgc ccctccctcc ccagctctcc atccctcacc ctctgtgctt
```

```
2641  ctgtctccat ccctggctct ccagcgtccc tggccttttg gtccctgagc tttaatgcct
2701  ttccctgcct tctgttctta tttggactgc agtggccctt gcaggagct  ctggaggccc
2761  aggggctgag gaggagggtt acccctctac ccatctgaaa cctagggtct aggggatca
2821  aggaaaaaaa gtccccaaag aagggaatt  ttttgtttgt ttttgagggg agatcccaga
2881  aatgtagctt gtttcatatt ttagtcttct tattttgta  aaatgtgtag aatttgctgt
2941  ttttcttttt cttttgacaa ctcaggaaga aactgacctc agaaagaatg ttagactttg
3001  gctgctctcc tgtgtgcccc tcacacctgc ccctccccc  ccactccatc caggggacca
3061  aattctccca gacactcaaa aaatgagact acggggaag  gggagaggaa gacccagagg
3121  cctcagtgaa accccagcta ttcctggtca gaagcagaat gtattcctaa gggcttcctc
3181  cccagggccg aggcctaggc atgaatgtgg ggagtgggct gtgggtttg  agagaaggga
3241  ggccttattc ctctcctgct gctccccacc ccctgcccca cccaacccct ccgctgagtg
3301  ttttctgtga agggctatcc agagttagga tgcccttgcc caattccttc ctgagaccca
3361  gaaggtaggg tgggagggc  caaatgggaa ggtgacctaa gcagaaagtc tccagaaagg
3421  tcatgtcccc tggccctgcc ttggcagagg tccccagtga cttatgctag gaggattcca
3481  tctgggtaga cagtctggcc acaaaatcag ctactggacc tcagccatct ctgctggagg
3541  ctctgaggag gagtgagcat ccctcacttg tggggctct  gtgaggaaat gtgccttccc
3601  cattccccg  gagtcctagg tctggagctc cagggctggg agagggtgag ggagatgggc
3661  agggtgtttt tctctgacct tgggggctta gtctcagtcc tgcctgaact ttccactagg
3721  cttggaaccc ttccaagaac catatttctc tccttcccac caatttccc  ttgatgaggc
3781  tttagcagtt tgctcccacc accccagcc  catttcacaa ctctgatctt agtccaaagc
3841  aggggacacg ccccccacc  accactttt  ctctctccca tctcagcctc ctgtgcagtt
3901  ccttgcctgc ccgtgcattt cctagagtct actgcctccc ccctggctgg gagggtgtct
3961  gggggggatc tttcaggggc cctggcaccc agggcctgtg ctggcctagg agtgctgacc
4021  agaaggctgc tctgttcccc cccaccccg  ttgctttctg gcccctctt  tggagccagc
4081  cacccacagg gctttggtgc ctcagaagca gtgggctgcc gggtcacagc cgcaggctgc
4141  aaaagaccct cggagggagc atggagtgag gggttctctc tcaggtgtgt atgtattggg
4201  gggtggggt  gggtggaggg tgtcagggaa gttggggtgg gatcccagcc ttcccttcaa
4261  gaggcaggga gctctgggag gtggagtccc caccgctttc tctactaggc tcctcctgtt
4321  ccccaggctt ggggagcttt gcacaaggag actgccccca gcctagtggc acctacctca
4381  tgggctctgg ggcaggtagg ggaagggcca gtccagctct ggtaatgctg gggggaggca
4441  taccaaagaa tccaggggca gggagtgggg agggtgactt ccgagctggc ctctcccctt
4501  cctctaccca gactggggct gggatcctct cctcccgctg taaccatttc tacctcattt
4561  tgctgcgtgt tgtacatgga cgtatttatc tcctgtctga cgatgctctg cagttgtggt
4621  ctgtctacct cagaagagac tgtatttaa  aagaaagtat tacacagtat taaagcgatg
4681  acatgtggtt tgcaaaaaaa aaaaaaaaaa a
``` which encodes:

(human Fidgetin-like 2)
(SEQ ID NO: 2)
MHWTPEHAQPLNQWPEQHLDVSSTTPSPAHKLELPPGGRQRCHYAWA

HDDISALTASNLLKRYAEKYSGVLDSPYERPALGGYSDASFLNGAKG

DPEPWPGPEPPYPLASLHEGLPGTKSGGGGGSGALGGSPVLAGNLPE

PLYAGNACGGPSAAPEYAAGYGGGYLAPGYCAQTGAALPPPPPAALL

QPPPPPGYGPSAPLYNYPAGGYAAQPGYGALPPPPGPPPAPYLTPGL

PAPTPLPAPAPPTAYGFPTAAPGAESGLSLKRKAADEGPEGRYRKYA

-continued

```
YEPAKAPVADGASYPAADNGECRGNGFRAKPPGAAEEASGKYGGGVP

LKVLGSPVYGPQLEPFEKFPERAPAPRGGFAVPSGETPKGVDPGALE

LVTSKMVDCGPPVQWADVAGQGALKAALEEELVWPLLRPPAYPGSLR

PPRTVLLFGPRGAGKALLGRCLATQLGATLLRLRGATLAAPGAAEGA

RLLQAAFAAARCRPPSVLLISELEALLPARDDGAAAGGALQVPLLAC

LDGGCGAGADGVLVVGTTSRPAALDEATRRRFSLRFYVALPDSPARG

QILQRALAQQGCALSERELAALVQGTQGFSGGELGQLCQQAAAGAG

LPGLQRPLSYKDLEAALAKVGPRASAKELDSFVEWDKMYGSGH.
```

In embodiments, the siRNA comprise one of the following pairs of sense/antisense sequences:

```
Sense:
                                        (SEQ ID NO: 3)
UUACACAGUAUUAAAGCGAUU Antisense:
                                        (SEQ ID NO: 4)
5' UCGCUUUAAUACUGUGUAAUU;
or Sense:
                                        (SEQ ID NO: 5)
CAUCUGAAACCUAGGGUCUUU Antisense:
                                        (SEQ ID NO: 6)
5' AGACCCUAGGUUUCAGAUGUU;
or Sense:
                                        (SEQ ID NO: 7)
GUGACUUAUGCUAGGAGGAUU Antisense:
                                        (SEQ ID NO: 8)
5' UCCUCCUAGCAUAAGUCACUU;
or Sense:
                                        (SEQ ID NO: 9)
GGUCAGAAGCAGAAUGUAUUU Antisense:
                                        (SEQ ID NO: 10)
5' AUACAUUCUGCUUCUGACCUU.
```

In an embodiment, the siRNA is double-stranded and comprises SEQ ID NO:3 and 4; SEQ ID NO:5 and 6; SEQ ID NO:7 and 8; or SEQ ID NO:9 and 10.

In an embodiment, the 5' terminal residue of a strand of the siRNA is phosphorylated. In an embodiment the 5' terminal residue of the antisense strand of the siRNA is phosphorylated.

As used herein an "aptamer" is a single-stranded oligonucleotide or oligonucleotide analog that binds to a particular target molecule, such as a Fidgetin-like 2 protein, or to a nucleic acid encoding a Fidgetin-like 2 protein, and inhibits the function or expression thereof, as appropriate. Alternatively, an aptamer may be a protein aptamer which consists of a variable peptide loop attached at both ends to a protein scaffold that interferes with Fidgetin-like 2 protein interactions The present invention provides kits for treating wounds, preferably skin wounds.

A composition provided in such a kit may be provided in a form suitable for reconstitution prior to use (such as a lyophilized injectable composition) or in a form which is suitable for immediate application to a wound, including to the wound margin, such as a lotion or ointment.

In an embodiment of the invention the inhibitor of fidgetin-like 2 is provided by a subcutaneous implant or depot medicament system for the pulsatile delivery of the inhibitor to a wound or site where a wound is to expected be formed to promote wound healing. The inhibitor can be provided, for example, in a therapeutically effective amount to each centimeter of a wound margin or each centimeter of a site at which a wound is expected to be formed.

A medicament in accordance with this aspect of the invention may be formulated in any appropriate carrier. Suitable carriers are pharmaceutically acceptable carriers, preferably those consistent with administration topically or administration by injection.

It will be appreciated that, while the inhibitor of Fidgetin-like 2 may be administered by the same route and in the same form in each incidence of treatment, different incidences of treatment may provide the inhibitor of Fidgetin-like 2 by different medicaments and/or different routes of administration. In embodiments of the invention the initial incidence of treatment may provide the inhibitor of Fidgetin-like 2 by means of an injection, such as an intradermal injection, while the second (and any subsequent) incidences of treatment may involve provision of the inhibitor of Fidgetin-like 2 by alternative routes, such as topical formulations, or vice versa. In an embodiment, multiple administrations of the inhibitor of Fidgetin-like 2 may be effected by the same means or route.

The benefits that may be derived from the present invention may be applicable to wounds at sites throughout the body. However, it may be preferred that the wound for which healing is promoted is a skin wound. For illustrative purposes the embodiments of the invention will generally be described with reference to skin wounds, although they remain applicable to other tissues and organs. Merely by way of example, in another preferred embodiment the wound may be a wound of the circulatory system, particularly of a blood vessel. Other wounds in which wound healing may be promoted in accordance with the present invention include as a result of surgery or as a result of a burn. Other wounds in which wound healing may be promoted in accordance with the present invention include skin ulcers caused by pressure, venous stasis, or diabetes mellitus.

In a non-limiting embodiment the inhibitor of Fidgetin-like 2 is provided in a bulk-eroding system such as polylactic acid and glycolic acid (PLGA) copolymer based microspheres or microcapsules systems containing the inhibitor of Fidgetin-like 2. In an embodiment, blends of PLGA:ethylcellulose systems may be used as an appropriate carrier. A further medicament in accordance with this aspect of the invention may be formulated in a surface-eroding system wherein the inhibitor of Fidgetin-like 2 is embedded in an erodible matrix such as the poly(ortho) ester and polyanhydride matrices wherein the hydrolysis of the polymer is rapid. A medicament in accordance with this aspect of the invention may also be formulated by combining a pulsatile delivery system as described above and an immediate release system such as a lyophilized injectable composition described above.

Examples of specific wounds in which healing may be promoted using the medicaments and methods of the invention include, but are not limited to, those independently selected from the group consisting of: wounds of the skin; wounds of the eye (including the inhibition of scarring resulting from eye surgery such as LASIK surgery, LASEK surgery, PRK surgery, glaucoma filtration surgery, cataract surgery, or surgery in which the lens capsule may be subject to scarring) such as those giving rise to corneal cicatrisation;

wounds subject to capsular contraction (which is common surrounding breast implants); wounds of blood vessels; wounds of the central and peripheral nervous system (where prevention, reduction or inhibition of scarring may enhance neuronal reconnection and/or neuronal function); wounds of tendons, ligaments or muscle; wounds of the oral cavity, including the lips and palate (for example, to inhibit scarring resulting from treatment of cleft lip or palate); wounds of the internal organs such as the liver, heart, brain, digestive tissues and reproductive tissues; wounds of body cavities such as the abdominal cavity, pelvic cavity and thoracic cavity (where inhibition of scarring may reduce the number of incidences of adhesion formation and/or the size of adhesions formed); and surgical wounds (in particular wounds associated with cosmetic procedures, such as scar revision). It is particularly preferred that the medicaments and methods of the invention be used to promote healing of wounds of the skin.

The inhibitor may be used in a composition with additives. Examples of suitable additives are sodium alginate, as a gelatinizing agent for preparing a suitable base, or cellulose derivatives, such as guar or xanthan gum, inorganic gelatinizing agents, such as aluminum hydroxide or bentonites (termed thixotropic gel-formers), polyacrylic acid derivatives, such as Carbopol®, polyvinylpyrrolidone, microcrystalline cellulose and carboxymethylcellulose. Amphiphilic low molecular weight and higher molecular weight compounds, and also phospholipids, are also suitable. The gels can be present either as water-based hydrogels or as hydrophobic organogels, for example based on mixtures of low and high molecular weight paraffin hydrocarbons and vaseline. The hydrophilic organogels can be prepared, for example, on the basis of high molecular weight polyethylene glycols. These gelatinous forms are washable. Hydrophobic organogels are also suitable. Hydrophobic additives, such as petroleum jelly, wax, oleyl alcohol, propylene glycol monostearate and/or propylene glycol monopalmitostearate, in particular isopropyl myristate can be included. In an embodiment the inhibitor is in a composition comprising one or more dyes, for example yellow and/or red iron oxide and/or titanium dioxide for the purpose of matching as regards color. Compositions may be in any suitable form including gels, lotions, balms, pastes, sprays, powders, bandages, wound dressing, emulsions, creams and ointments of the mixed-phase or amphiphilic emulsion systems (oil/water-water/oil mixed phase), liposomes and transfersomes or plasters/band aid-type coverings. Emulsifiers which can be employed in compositions comprising the inhibitor of Fidgetin-like 2 include anionic, cationic or neutral surfactants, for example alkali metal soaps, metal soaps, amine soaps, sulphonated and sulphonated compounds, invert soaps, higher fatty alcohols, partial fatty acid esters of sorbitan and polyoxyethylene sorbitan, e.g. lanette types, wool wax, lanolin or other synthetic products for preparing the oil/water and/or water/oil emulsions.

Compositions comprising the inhibitor of Fidgetin-like 2 can also comprise vaseline, natural or synthetic waxes, fatty acids, fatty alcohols, fatty acid esters, for example as monoglycerides, diglycerides or triglycerides, paraffin oil or vegetable oils, hydrogenated castor oil or coconut oil, hog fat, synthetic fats (for example based on caprylic acid, capric acid, lauric acid or stearic acid, such as Softisan®), or triglyceride mixtures, such as Miglyol®, can be used as lipids, in the form of fatty and/or oleaginous and/or waxy components for preparing the ointments, creams or emulsions of the compositions comprising the inhibitor of fidgetin-like 2 used in the methods described herein.

Osmotically active acids and alkaline solutions, for example hydrochloric acid, citric acid, sodium hydroxide solution, potassium hydroxide solution, sodium hydrogen carbonate, may also be ingredients of the compositions and, in addition, buffer systems, such as citrate, phosphate, tris buffer or triethanolamine, for adjusting the pH. It is possible to add preservatives as well, such as methyl benzoate or propyl benzoate (parabens) or sorbic acid, for increasing the stability.

Pastes, powders and solutions are additional forms of compositions comprising the inhibitor of Fidgetin-like 2 which can be applied topically. As consistency-imparting bases, the pastes frequently contain hydrophobic and hydrophilic auxiliary substances, preferably, however, hydrophobic auxiliary substances containing a very high proportion of solids. In order to increase dispersity, and also flowability and slipperiness, and also to prevent agglomerates, the powders or topically applicable powders can, for example, contain starch species, such as wheat or rice starch, flame-dispersed silicon dioxide or siliceous earth, which also serve as diluent.

In an embodiment, the compositions comprise further active ingredients suitable for protecting or aiding in healing of the wound, for example one or more antibiotics, antiseptics, vitamins, anesthetics, antihistamines, anti-inflammatory agents, moisturizers, penetration-enhancing agents and/or anti-irritants.

In an embodiment of the methods and compositions described herein the subject is a mammal. In an embodiment the subject is human.

As used herein, "promotion" of wound healing, or grammatical equivalent, means an acceleration in any one or more of visual appearance of wound recovery, reduction in wound size, reduction in distance between wound margins, scab formation, fibroplasia and re-epithelialization as compared to the corresponding parameter in an untreated wound.

As used herein, "wound" is a break or discontinuity in the structure of an organ or tissue (including skin), which includes epithelium, connective tissue, and muscle tissue, caused by an external agent. Examples of wounds include, but are not limited to, skin wounds, ulcerations, bedsores, grazes, tears, cuts, punctures, tympanic membrane perforations, burns, and those that are a consequence of plastic surgery procedures.

With regard to the methods described herein to identify candidate agents as inhibitors of Fidgetin-like 2, one skilled in the art can readily screen libraries of compounds, for example small molecule libraries, using the methods as described to identify agents which are inhibitors of Fidgetin-like 2 and which are therapeutic in treating wounds and promoting the healing of wounds. In addition, one skilled in the art can employ the method to identify peptides, peptidomimetics, antibodies, antibody fragments and nucleic acids which are inhibitors of Fidgetin-like 2 and which are therapeutic in treating wounds and promoting the healing of wounds.

The method can be employed as an assay using detection and quantification techniques known in the art, including those pertaining to measuring enzyme activity, such as the ATPase activity of Fidegtin-like 2.

The methods can be used to identify inhibitors of Fidgetin-like 2 which can then be applied to wound models to determine if the agent promotes/accelerates wound healing, especially for skin.

Preferably the inhibitor is biomembrane-permeable or is conjugated or otherwise attached to a moiety which renders the inhibitor biomembrane-permeable.

A method is also provided for treating wound in a subject comprising administering to the subject an amount of an inhibitor of Fidgetin effective to treat the wound. In an embodiment, the inhibitor of Fidgetin is a nucleic acid. In an embodiment, the inhibitor of Fidgetin is an siRNA or shRNA. In an embodiment, the nucleic acid is directed against a DNA or mRNA encoding Fidgetin. In an embodiment, the Fidgetin is human Fidgetin. In an embodiment, the wound is a neuronal wound. In an embodiment, the inhibitor of Fidgetin is encapsulated in a nanoparticle. In an embodiment, the nanoparticle is a liposomal nanoparticle. In an embodiment, the Fidgetin comprises the following sequence:

```
                                              (SEQ ID NO: 11)
  1     MISSTSVYGL KMQWTPEHAQ WPEQHFDITS TTRSPAHKVE
        AYRGHLQRTY QYAWANDDIS

61     ALTASNLLKK YAEKYSGILE GPVDRPVLSN YSDTPSGLVN
        GRKNESEPWQ PSLNSEAVYP

121     MNCVPDVITA SKAGVSSALP PADVSASIGS SPGVASNLTE
        PSYSSSTCGS HTVPSLHAGL

181     PSQEYAPGYN GSYLHSTYSS QPAPALPSPH PSPLHSSGLL
        QPPPPPPPPP ALVPGYNGTS

241     NLSSYSYPSA SYPPQTAVGS GYSPGGAPPP PSAYLPSGIP
        APTPLPPTTV PGYTYQGHGL

301     TPIAPSALTN SSASSLKRKA FYMAGQGDMD SSYGNYSYGQ
        QRSTQSPMYR MPDNSISNTN

361     RGNGFDRSAE TSSLAFKPTK QLMSSEQQRK FSSQSSRALT
        PPSYSTAKNS LGSRSSESFG

421     KYTSPVMSEH GDEHRQLLSH PMQGPGLRAA TSSNHSVDEQ
        LKNTDTHLID LVTNEIITQG

481     PPVDWNDIAG LDLVKAVIKE EVLWPVLRSD AFSGLTALPR
        SILLFGPRGT GKTLLGRCIA

541     SQLGATFFKI AGSGLVAKWL GEAEKIIHAS FLVARCRQPS
        VIFVSDIDML LSSQVNEEHS

601     PVSRMRTEFL MQLDTVLTSA EDQIVVICAT SKPEEIDESL
        RRYFMKRLLI PLPDSTARHQ

661     IIVQLLSQHN YCLNDKEFAL LVQRTEGFSG LDVAHLCQEA
        VVGPLHAMPA TDLSAIMPSQ

721     LRPVTYQDFE NAFCKIQPSI SQKELDMYVE WNKMFGCSQ.
```

In an embodiment, the Fidgetin is encoded by a nucleic acid sequence comprising the following:

```
                                              (SEQ ID NO: 12)
   1    gggtttgaaa ttccaacatg gcagaggctg cagtccgtct tcccttcaaa aacttggaat
  61    gatttcaaat cataggcacc ttcacttaac cctagcttcc attcatcagc aaacacatcg
 121    gatcgatgct acgctaacct atcgggttct ctctccgcgc gttcaggtta aatgaatacc
 181    tgacgaaagg gcccacgttt caaggcagtg acatttgata gctgagagga aaagtggctt
 241    taatgaaaag caacctttgg aattcctgct tgtgagaaat ccaattcagc ttttgtgct
 301    gccagcaaga aatgatcagt agcaccagtg tttatggctt gaagatgcag tggacgccag
 361    agcatgccca gtggccagaa cagcactttg acatcacctc aaccactcgg tctcctgccc
 421    acaaagttga agcctacaga ggtcatctgc agcgcaccta tcagtacgcc tgggcgaatg
 481    atgacatatc tgctctgact gcatccaacc tactaaaaaa atatgcagag aagtattccg
 541    gcattttgga aggtcctgtg gaccgacccg tactcagcaa ctattcggac acaccatcag
 601    gactagtgaa cggtcggaaa aatgaaagtg aaccctggca gccttccttg aattcagaag
 661    ctgtttatcc catgaactgt gttccggatg ttatcactgc cagcaaagct ggagtcagtt
 721    cagccctccc tccagcagat gtctctgcga gtataggaag ctctcctggg gtagccagca
 781    acctgacaga acctagttat tcaagtagta cctgtggaag ccacactgta cccagtcttc
 841    atgcagggct cccatctcag gaatatgccc caggatacaa cggatcatat tgcattcta
 901    cttatagtag ccagccagca cctgcacttc cttcacctca tccgtctcct ttgcatagct
 961    ctgggctact acagccccca ccaccacctc ctccgccacc agccttggtc ccaggctaca
1021    atgggacttc taacctctcc agttacagct atccgtctgc tagctatcct cctcagactg
1081    ctgtggggtc tgggtacagc cctgggggg caccgcctcc gccttcagcg tacctgcctt
1141    caggaattcc tgctcccacc ccctacccc ccaccactgt tcctggctac acctaccagg
1201    gccatggttt gacacctatt gcaccgtcgg ctctgacaaa cagttcagca agttctctca
1261    aaaggaaagc tttctacatg gcagggcaag gagatatgga ctccagttat ggaaattaca
1321    gctatggcca acagagatct acacagagtc ctatgtacag aatgcccgac aacagcattt
1381    caaacacaaa tcgggggaat ggctttgaca gaagtgctga acatcatcc ttagcattta
1441    agccaacgaa gcagctaatg tcctctgaac agcaaaggaa attcagcagc cagtccagta
```

-continued

```
1501  gggctctgac ccctccttcc tacagtactg ctaaaaattc attgggatca agatccagtg
1561  aatcctttgg gaagtacaca tcgccagtaa tgagtgagca tggggacgag cacaggcagc
1621  tcctctctca cccaatgcaa ggccctggac tccgtgcagc tacctcatcc aaccactctg
1681  tggacgagca actgaagaat actgacacgc acctcatcga cctggtaacc aatgagatta
1741  tcacccaagg acctccagtg gactggaatg acattgctgg tctcgacctg gtgaaggctg
1801  tcattaaaga ggaggtttta tggccagtgt tgaggtcaga cgcgttcagt ggactgacgg
1861  ccttacctcg gagcatcctt ttatttggac ctcggggac aggcaaaaca ttattgggca
1921  gatgcatcgc tagtcagctg ggggccacat ttttcaaaat tgccggttct ggactagtcg
1981  ccaagtggtt aggagaagca gagaaaatta tccatgcctc ttttcttgtg gccaggtgtc
2041  gccagccctc ggtgattttt gttagtgaca ttgacatgct tctctcctct caagtgaatg
2101  aggaacatag tccagtcagt cggatgagaa ccgaatttct gatgcaactg dacactgtac
2161  taacttcggc tgaggaccaa atcgtagtaa tttgtgccac cagtaaacca aagaaaatag
2221  atgaatccct tcggaggtac ttcatgaaac gactttaat cccacttcct gacagcacag
2281  cgaggcacca gataatagta caactgctct cacagcacaa ttactgtctc aatgacaagg
2341  agtttgcact gctcgtccag cgcacagaag ctttcctgg actagatgtg gctcatttgt
2401  gtcaggaagc agtggtgggc ccctccatg ccatgccagc cacagacctt tcagccatta
2461  tgcccagcca gttgaggccc gttacatatc aagacttga aaatgctttc tgcaagattc
2521  agcctagcat atctcaaaag gagcttgata tgtatgttga atggaacaaa atgtttggtt
2581  gcagtcagtg ataacttctt tagaaaaaaa aaatgtaatg aatgttggca cacacacata
2641  aaacctgcta catagggaat agagccctt tccagtagag tttaaattgc aaagggtact
2701  ggggaagatg acgattaagt tgcatcttta gagtcagggt agatttggag gaaaagtgca
2761  tcaaatgaga gcttctgatt tgaaagcccc agatgacaga aagcatatgt ggatgctcag
2821  ttctgttcaa gctagacaac actcaccaag gagcaaggtg caagtgtgtt gatttcagaa
2881  ggacatgaac ctcgtgtgtt gattccattc tgctgttctc gagatttagt tgctgtcaag
2941  tgcctggagt ggtgctttat tttttgtttg cctcacaatt acattggtgg catgtgctaa
3001  tataaagagc tttaacttca aacattattg gactaaagag atgaacagtt gtgttatgac
3061  agaaaaccag atttttgcca ttttaagagc aacagtattc ctcaatcctg tctgttctgc
3121  agtattaagc taagaacagg taaaacaggg taacggtaat ctggaccta atttctgcag
3181  ttcatttctt ttaatgttct tgtctgcaaa aactcaggaa agtgattgtg atttgtacag
3241  tacctcaaag gaatgtgttg aaagcactat gtactgctga gagtaatagg ataggcttca
3301  atgttacttt atattaaaat gtatgtttac ctcaacaatt ggaaaatagc aaggaaaatt
3361  actttgaatg tatccagaaa aatactgaag tgtgatacaa ctgaatattt acagtttaaa
3421  gtagaaatgg aaggattttt ttaagttctt ttactaatta tggggaatta accagagcag
3481  aataattctt tatgtcaata actgcaagag ttcttagtac attgctcctt gataattaag
3541  tgaaaatgtt cttaaaaggt acactggtta attgaaagct acttattcag tttgtgttag
3601  tgtctagacc tgtcagccac aagacctgtt taggaccctg aaagtcacag tacctaaaaa
3661  ctatgactgc cttttattg cataggtggt agtggtggtg atggtggtgg tagtttgcaa
3721  gttatctctt aaaactgctg ggaatggtgt cattctattc actaatctag cttatagact
3781  tgccgtgctg tttgatagaa tgcagaggat agcaaccaaa acaaatacac aaataaataa
3841  aaacaaaaac caaccaacaa accaacttac atacacatat atatatccac aaagaacctc
3901  tccatctcct cccttctttt ttgactccac tcttgtcagt gcaatttgc ttctcatttt
```

```
3961  gaaatctggg ctgtagtgct cctgctttat ttctacctca gttttgttac atttctcttg 4021  gaaagtaaag tagaaaattg gaagtggaca cacacactgc aatgtagctt gccaaacatg 4081  ttactttgtt ttcttccatc tttcaccgta aatctagttt ccaaagacat cagcatttgt 4141  gcttacttcc acctcagtct accagcccca cccctaccca tggcataagt ggcatttttc 4201  ttaatttcct attttttctcc tgctctctgt caagttgttc tttgtatcct ttaatgcttt 4261  atgtgcaacc tttcattgat agtgggctga tgtttggcaa tgcttctgaa ctgtcacaga 4321  gcaggctgta gctttccaca gccactgccc atgcataagc agaacagcct ggccttttga 4381  atgtattttc ctgggttttt tccccttttc tttttttagt ttagagatgc agtaacaaaa 4441  ctgttgcaaa gcactggcat tttatgtatt caataaataa gtgatgtaca tttttaaaaa 4501  aatttaaata aatgcaatga gaagcccaa gaaag
```

All combinations of the various elements described herein are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Introduction

At present, papers have not been published on human Fidgetin-like 2, but the mouse homologue has been found to be highly expressed in most tissues (with the exception of testes) (Yang, Mahaffey et al. 2005). However, this laboratory has now identified the following role for human Fidgetin-like 2.

Results

Fidgetin-like 2 is expressed in human tissue culture cells where it localizes to microtubules. FIG. 1A shows a Western blot of human U2OS cell lysates probed with an anti-Fidgetin-like 2 antibody generated in lab. This antibody recognizes a single band that is substantially decreased by Fidgetin-like 2 siRNA treatment (see FIG. 2 below). FIG. 1B shows a migrating U2OS cell double-labeled for Fidgetin-like 2 and microtubules. At high magnification (inset), Fidgetin-like 2 clearly co-localizes with spans of the microtubule lattice near the cell edge.

Figures 2A, 2B, 2C, 2D, 2E:
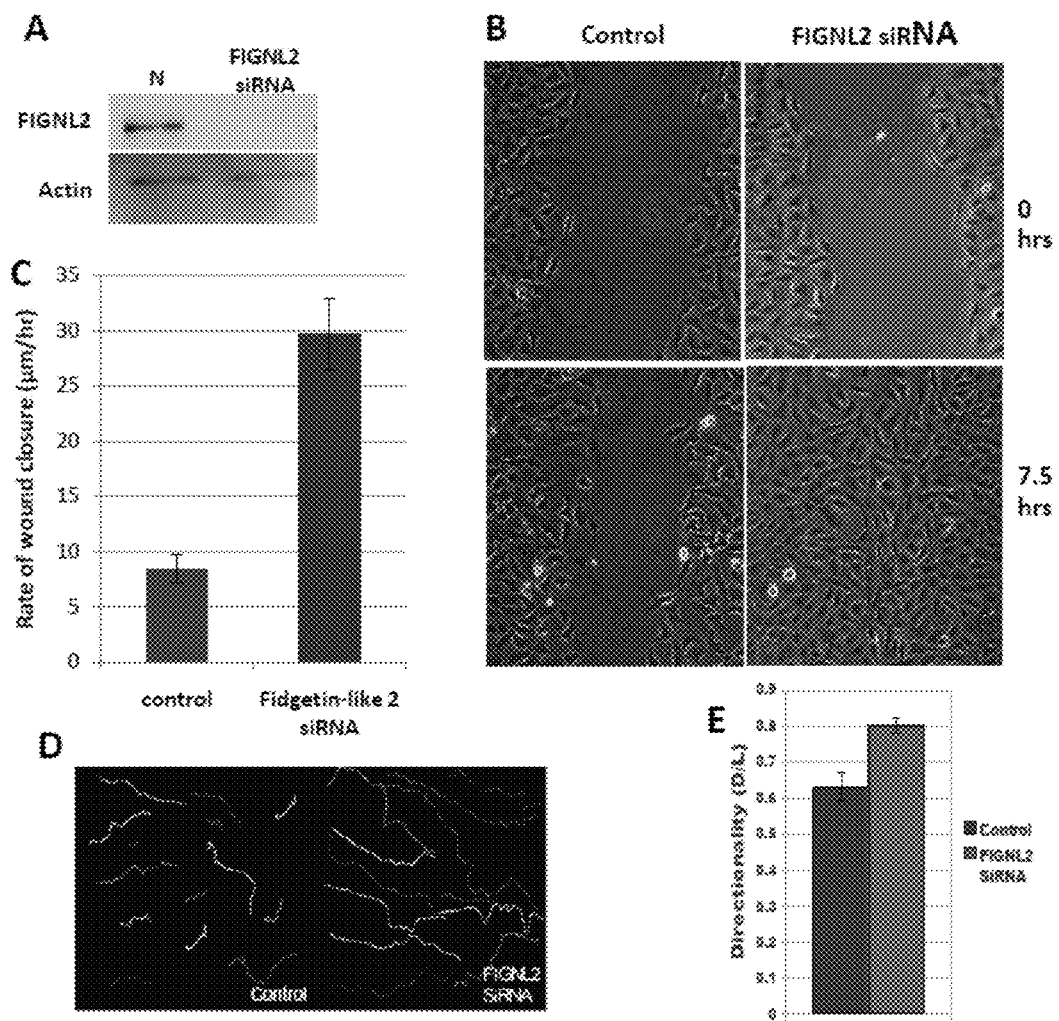
FIG. 2A-2E: Cells depleted of Fidgetin-like 2 display a several-fold increase in their rate of wound healing and migration.

Cells depleted of Fidgetin-like 2 display a several-fold increase in their rate of wound healing and migration (FIG. 2). FIG. 2A shows Western blots of U2OS cell lysates obtained from control (N) and Fidgetin-like 2 siRNA treated cultures (72 hrs after treatment). Actin was used as a loading control. FIG. 2B shows time-lapse phase contrast images of "wound healing" assays performed in control and Fidgetin-like 2 siRNA treated cultures. In these assays, a monolayer of U2OS cells is "wounded" by a pipette tip and the invasion of cells into the wound is monitored over time. FIG. 2C shows the average rate of wound closure in each condition which is increased nearly 4-fold after Fidgetin-like 2 siRNA. FIG. 2D shows the trajectories of single control and Fidgetin-like 2 siRNA treated cells as they enter the wound zone. Not only do Fidgetin-like 2 siRNA-treated cells move several-fold faster than controls, they also display more directionally persistent migration as indicated in FIG. 2E.

Figure 3:
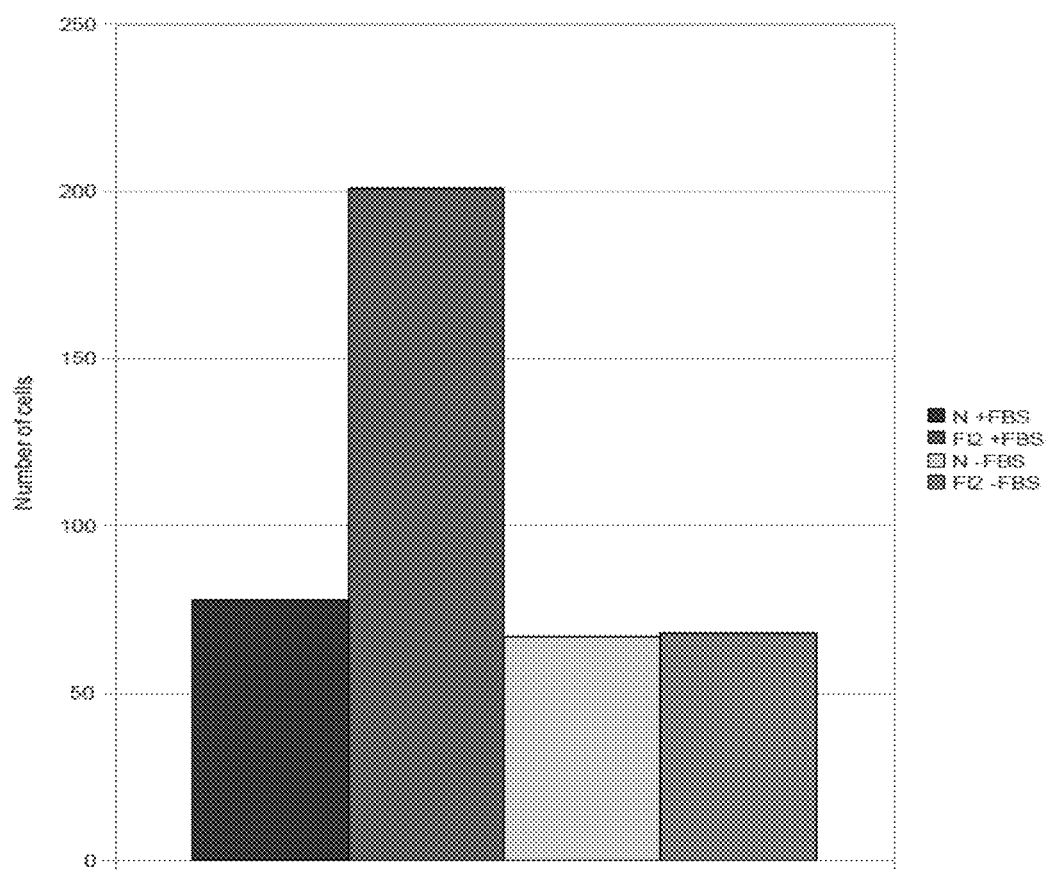
FIG. 3: Fidgetin-like 2 siRNA also dramatically enhances chemotaxis of cultured human cells. The impact of Fidgetin-like 2 siRNA on chemotaxis of human U2OS cells was measured in a transwell assay (modified Boyden chamber). This assay counts the number of cells that move through 8 μm pores towards a chemoattractant loaded in the distal well. The graph in FIG. 3 shows the number of control (N) and siRNA-treated (F12) cells that migrated through the pores before and three hours after the addition of a chemoattractant (Fetal Bovine Serum).

Fidgetin-like 2 siRNA also dramatically enhances chemotaxis of cultured human cells (FIG. 3). The impact of Fidgetin-like 2 siRNA on chemotaxis of human U2OS cells was measured in a transwell assay (modified Boyden chamber). This assay counts the number of cells that move through 8 μm pores towards a chemoattractant loaded in the distal well. The graph in FIG. 3 shows the number of control (N) and siRNA-treated (F12) cells that migrated through the pores before and three hours after the addition of a chemoattractant (Fetal Bovine Serum).

Figure 4:
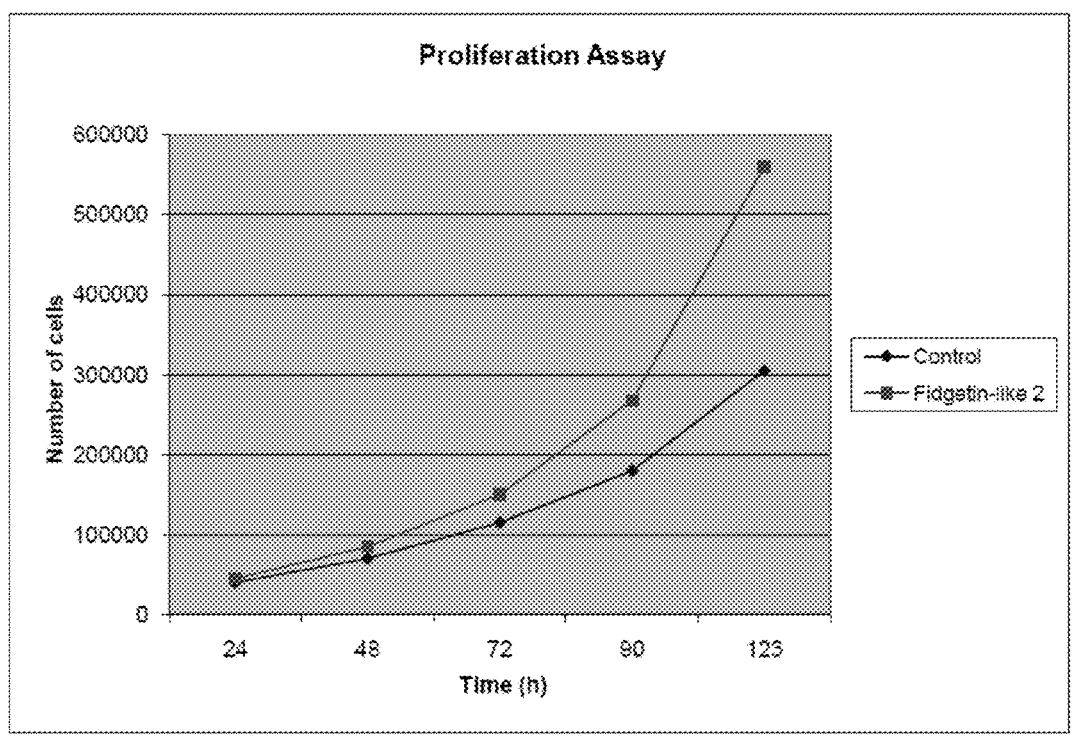
FIG. 4: siRNA directed to Fidgetin-like 2 elevates the rate of U2OS cell proliferation.
Figure 5:
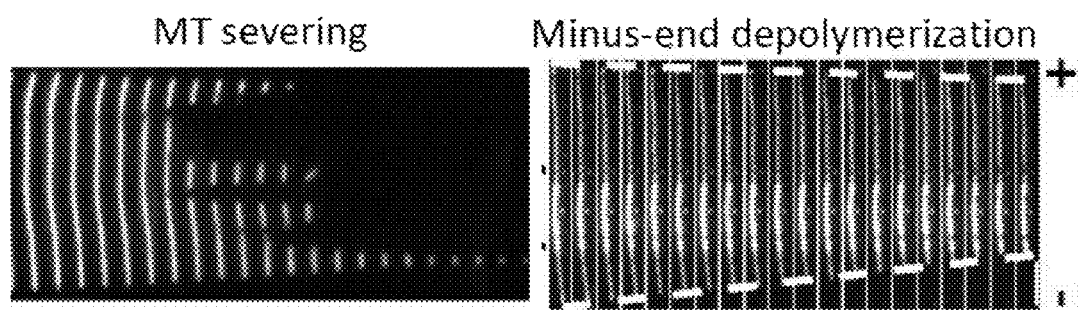
FIG. 5: Kymographs showing (left) severing of a MT incubated 50 nM recombinant Fidgetin and (right) depolymerization at the minus-end of a polarity marked induced MT incubated with 25 nM Fidgetin. ATP was added in both conditions. The reaction is entirely inhibited by the non-hydrolyzable ATP analogue, AMPPNP.
Figure 6:
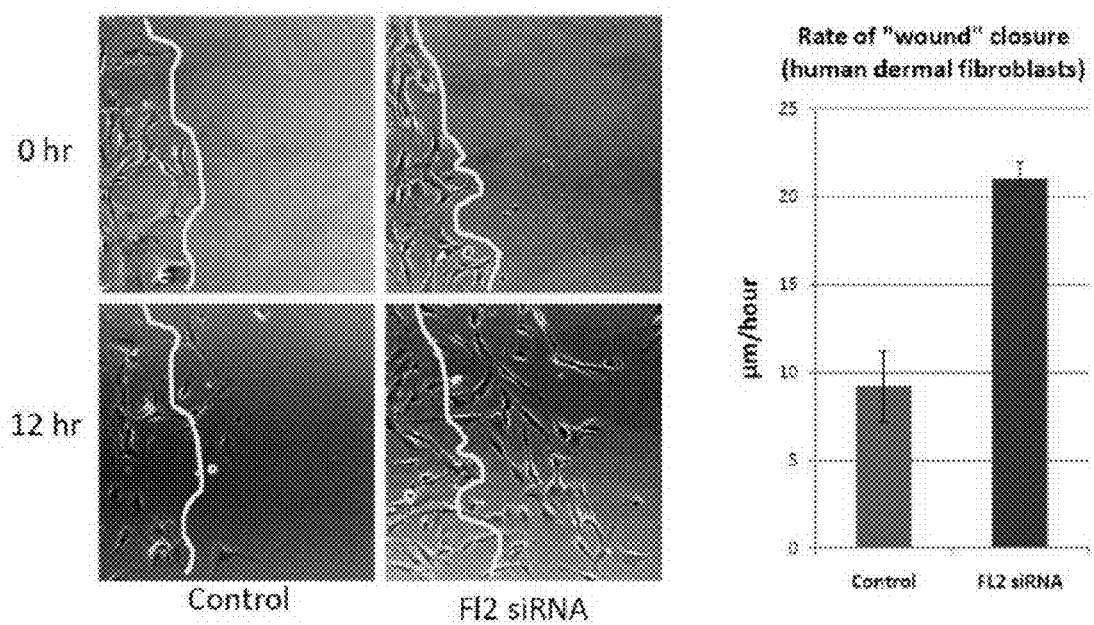
FIG. 6: Left panels show time-lapse phase contrast images of "wound healing" assays performed in control and Fidgetin-like 2 siRNA treated cultures of human dermal fibroblasts. In these assays, a monolayer is "wounded" by a pipette tip and the invasion of cells into the wound is monitored over time. The right panel shows the average rate of wound closure measured in each condition.

Fidgetin-like 2 siRNA elevates the rate of U2OS cell proliferation (FIG. 4). Although the biochemical activity of Fidgetin-like 2 has not been previously demonstrated, we have found that the closely related protein, Fidgetin, utilizes ATP hydrolysis to induce microtubule severing and depolymerization, in vitro (FIG. 5). FIG. 5 shows kymographs showing (left panel) severing of a MT incubated 50 nM recombinant Fidgetin and (right panel) depolymerization at the minus-end of a polarity marked induced MT incubated with 25 nM Fidgetin. ATP was added in both conditions. The reaction is entirely inhibited by the non-hydrolyzable ATP analogue, AMPPNP The studies of Fidgetin-like 2 were repeated in human dermal fibroblasts (adult). Fibroblasts depleted of Fidgetin-like 2 displayed a >2-fold increase in the rate of "wound closure" as determined by a standard scratch assay (see FIG. 6). The left panels of FIG. 6 show time-lapse phase contrast images of "wound healing" assays performed in control and Fidgetin-like 2 siRNA-treated cultures of human dermal fibroblasts. In these assays, a monolayer is "wounded" by a pipette tip and the invasion of cells into the wound is monitored over time. The right panel of FIG. 6 shows the average rate of wound closure measured in each condition.

Figures 7A, 7B:
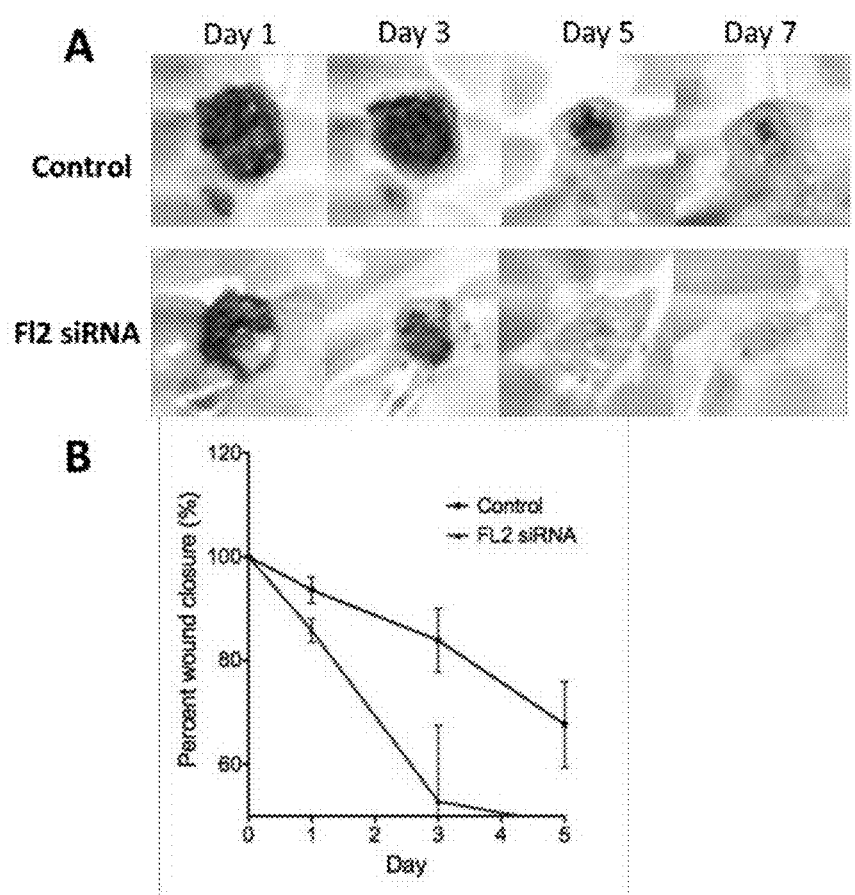
FIG. 7A-7B: Topical application of Fidgetin-like 2 siRNA encapsulated in nanpoparticles (np-si) increases the rate of wound closure in vivo. A) Images showing the closure of control and Fidgetin-like 2 np-si treated full thickness biopsy wounds positioned next to one another on the flank of a mouse. B) Plot showing the average rate of wound closure from each condition (n=3). Error bars are SEM. Wound closure is plotted to 50% because smaller wounds are difficult to measure with accuracy.
Figure 8:
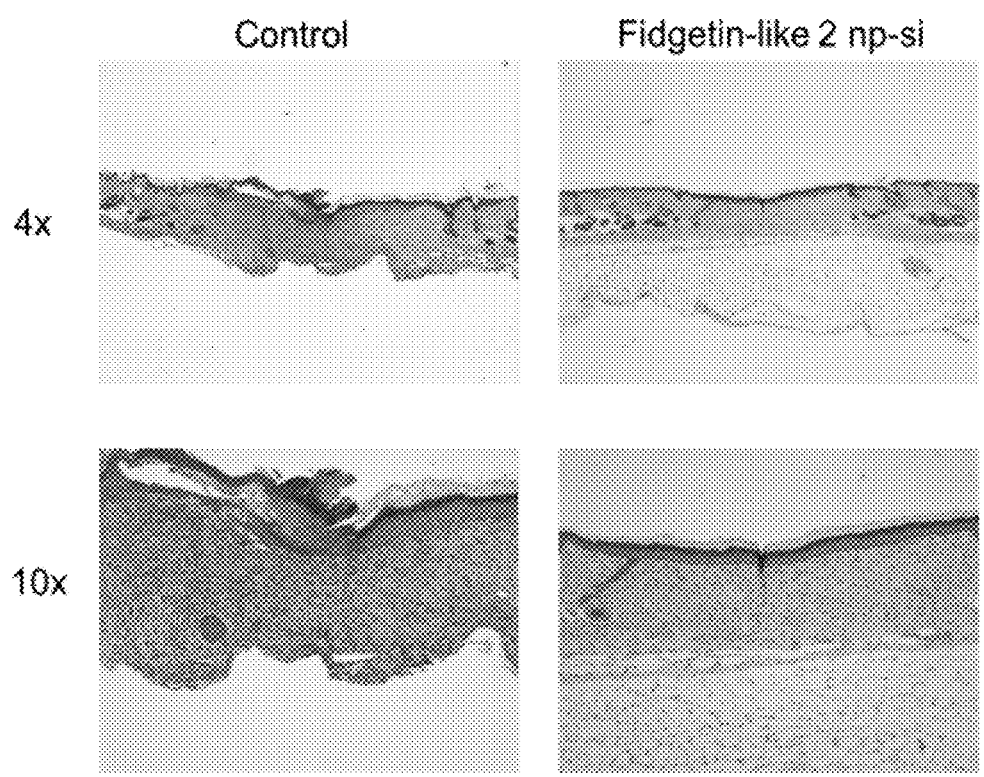
FIG. 8: Histology of Control and Fidgetin-like 2 np-si treated mouse biopsy wounds: Hematoxylin and Eosin staining of 5 mm punch biopsy wounds, mouse skin, day 9 after wounding. Control wounds (left) demonstrate a thin layer of re-epitheliazed epidermis with mounds of serum crust overlying. The dermis is composed of inflammatory, disorganized granulation tissue without evidence of subcutis. Fidgetin-like 2 np-si treated wounds demonstrate a completely re-epithelialized epidermis with overlying organized basket weaving stratum corneum. The dermis is devoid of intense inflammation and is infiltrated with parallel fibroblasts. There is a healthy appearing subcutis present.
Figure 9:
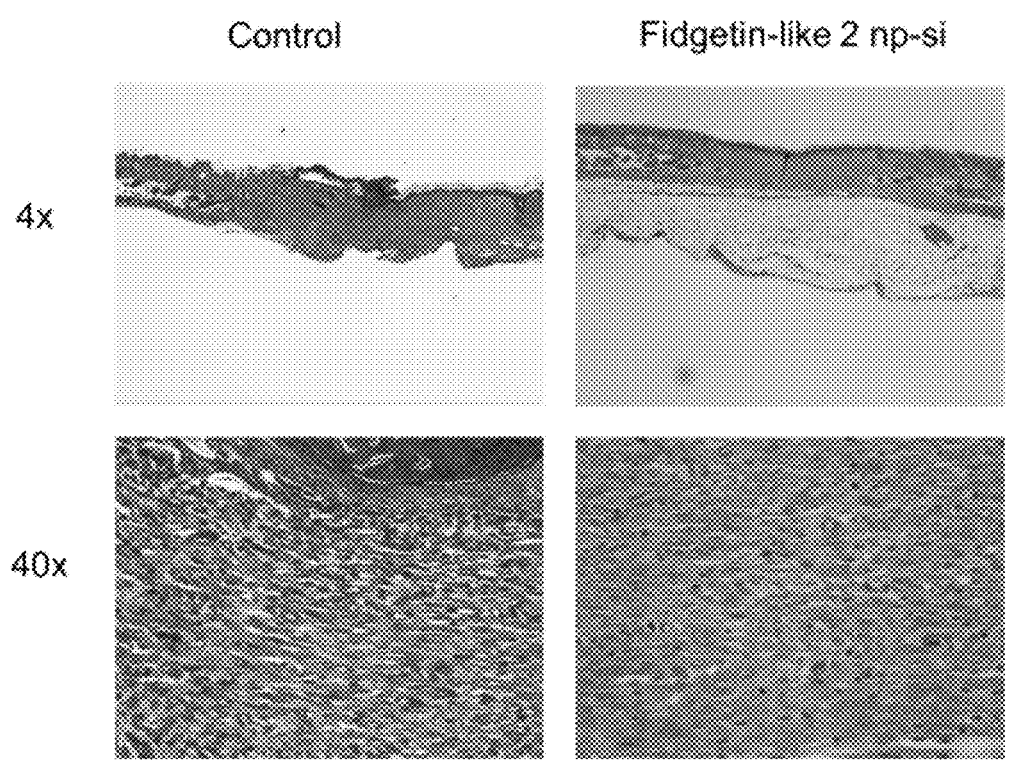
FIG. 9: Trichome masson staining for collagen reveal a necrobiotic degenerating collagen with minimal pale, newly deposited collagen present in the wound bed in the control (left) wound. In the Fidgetin-like 2 np-si treated wound, minimal cell death (as indicated by red) is noted and homogenous newly formed collagen (light blue) is noted.
Figure 10:
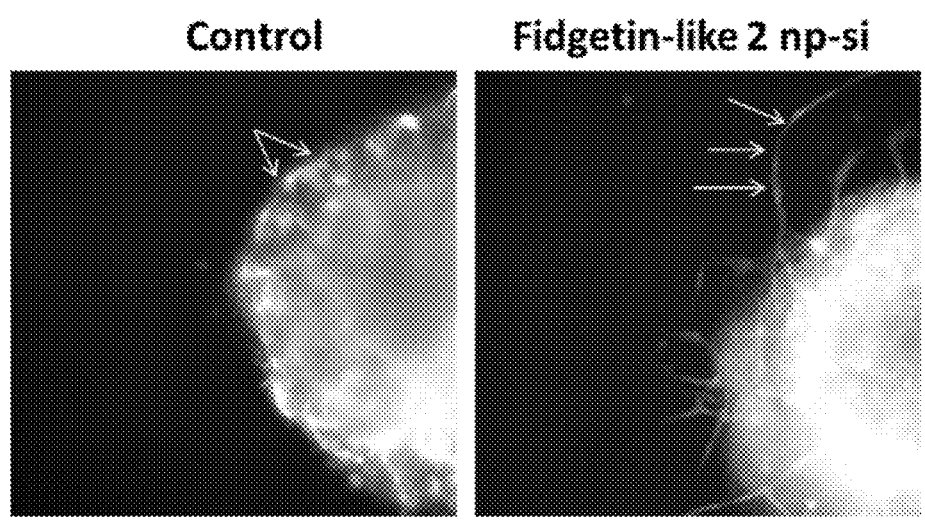
FIG. 10: Neoangiogenesis in embryonic hearts treated with Control or Fidgetin-like 2 np-si. Images show representative control and Fidgetin-like 2 np-si treated hearts three days after np-si treatment. In the control, migrating endocarial cells (GFP-labeled) have penetrated the ventricular wall (arrows) and will undergo angiogenesis over the next several days. By contrast, Fidgetin-like 2 np-si treatment dramatically promotes the angiogenic process by the endocardial cells, which have already formed a fine vascular network at this time point (arrows).
Figure 11:
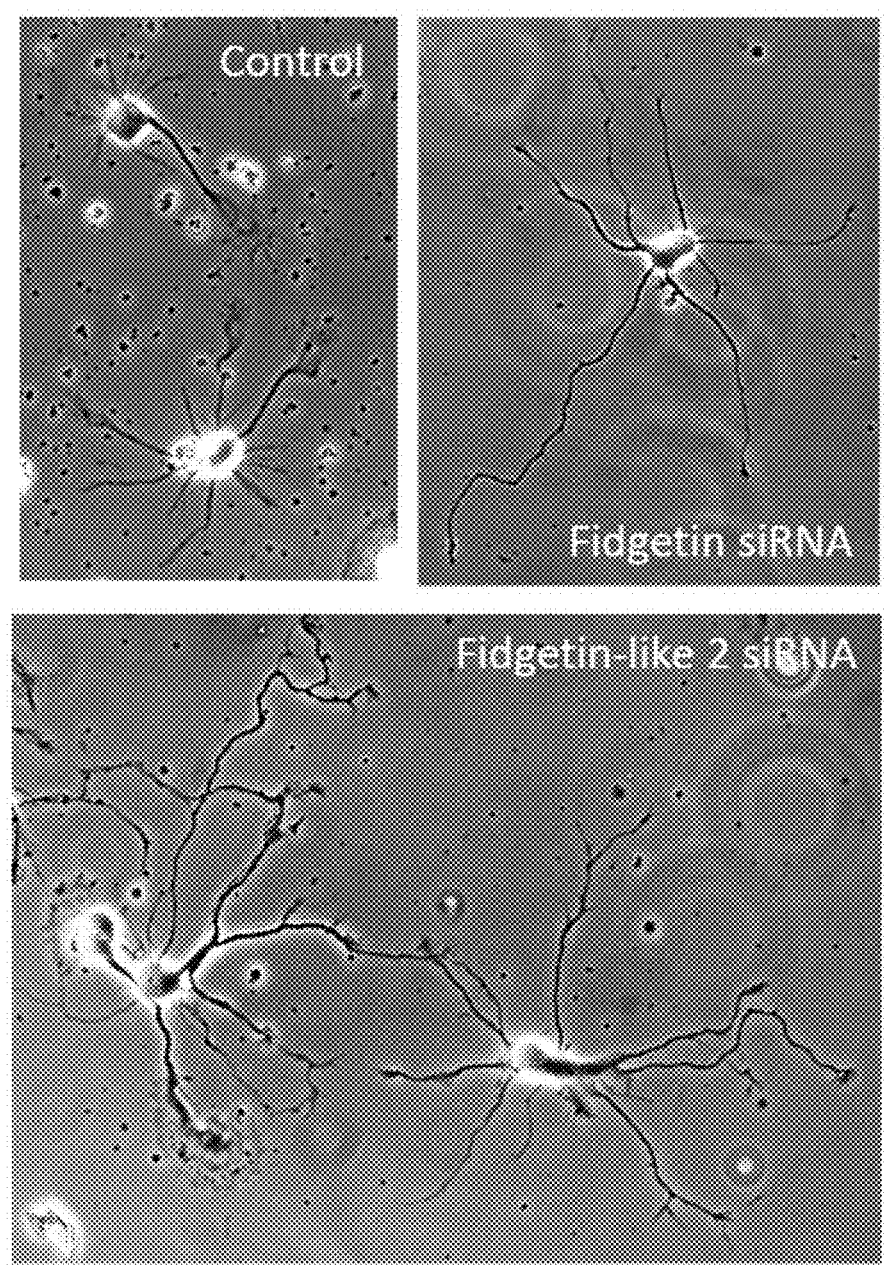
FIG. 11: Fidgetin and Fidgetin-like 2 siRNA nanoparticles strongly promote axon regrowth from hippocampal neurons. Images show dissociated rat hippocampal neurons 48 hours after siRNA treatment. (A similar effect was observed after 24 hours; not shown).
Figure 12:
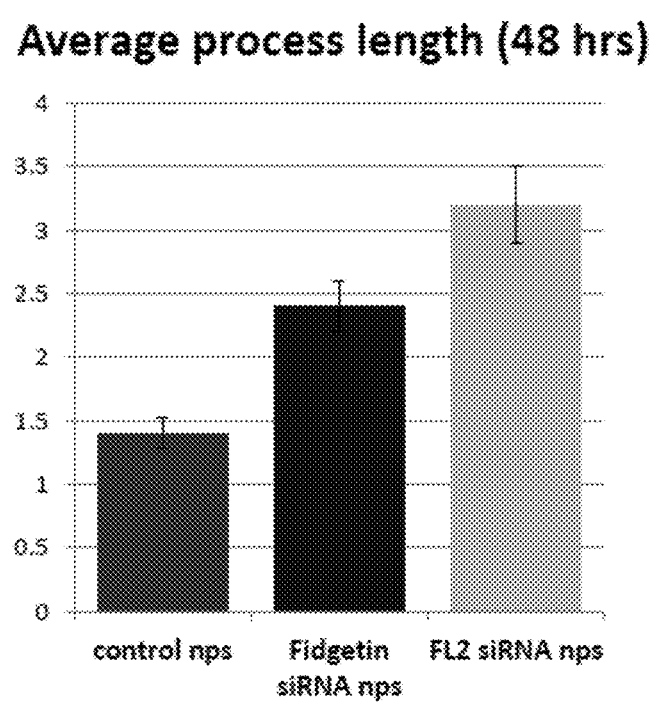
FIG. 12: Graphical representation showing Fidgetin and Fidgetin-like 2 siRNA nanoparticles strongly promote axon regrowth from hippocampal neurons.
Figure 13:
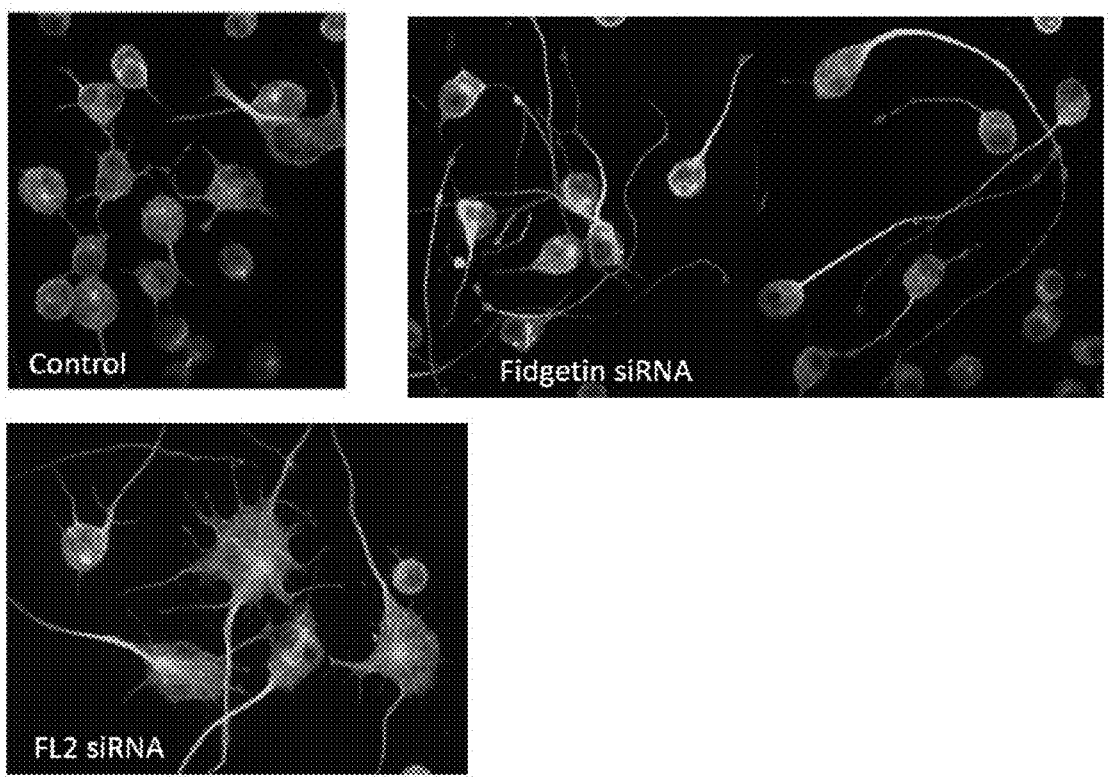
FIG. 13: Fidgetin and Fidgetin-like 2 siRNA nanoparticles promote axon growth and differentiation in N2A neuroblastoma cells (cells stained for microtubules).

In further experiments, topical application of Fidgetin-like 2 siRNA (encapsulated in nanoparticles) to mouse full thickness biopsy wounds was found to enhance wound healing (FIGS. 7, 8 and 9). In addition, depletion of Fidgetin-like 2 from embryonic mouse hearts was found to stimulate neoangiogenesis (FIG. 10). Furthermore, depletion of Fidgetin, and depletion of Fidgetin-like 2 from rat primary hippocampal neurons were both found to promote axon regrowth (FIGS. 11, 12 and 13).

EXAMPLE

A skin wound in a human subject is treated with a topically applied siRNA or shRNA which inhibits Fidgetin-like 2. The topically applied siRNA or shRNA is effective to treat the skin wound in the human subject. The topically applied siRNA or shRNA accelerates skin wound healing in the human subject.

REFERENCES

Yang, Y., C. L. Mahaffey, et al. (2005). "Functional characterization of fidgetin, an AAA-family protein mutated in fidget mice." Exp Cell Res 304(1): 50-58.

What is claimed is:

1. A method of reducing a scar comprising directly administering to the scar an amount of a siRNA or shRNA directed against a DNA or RNA encoding a human Fidgetin like-2 comprising the amino acid set forth in SEQ ID NO:2 effective to reduce a scar.

2. A method of stimulating neoangiogenesis in a tissue comprising directly administering to the tissue an amount of a siRNA or shRNA directed against a DNA or RNA encoding a human Fidgetin like-2 comprising the amino acid set forth in SEQ ID NO:2 effective to stimulate neoangiogenesis in a tissue.

* * * * *

SEQUENCE LISTING

<160> NUMBER OF SEQ ID NOS: 12

<210> SEQ ID NO 1
<211> LENGTH: 4711
<212> TYPE: DNA
<213> ORGANISM: HOMO SAPIENS

<400> SEQUENCE: 1

| | | | | |
|---|---|---|---|---|
| agtgagctat | ggggacacta | ctgcactgta | gcctgggcaa cagagcaaga | ccttgtctca | 60 |
| aaaatgtata | tatattttgg | gcttttttc | ctaaaacggg aactacaaca | gcatatttgc | 120 |
| gagctgatga | gagtgaccca | gcagagaggg | aaatggatca gctctgttga | agatgcactg | 180 |
| gacaccagaa | cacgcccagc | ccctcaacca | gtggccagag cagcacctgg | acgtctcctc | 240 |
| caccaccccg | tcgccggccc | acaagttgga | gttgccccct ggggtcgcc | aacgctgcca | 300 |
| ctacgcttgg | gcacacgacg | acatctcagc | cctcactgcc tccaacctcc | taaagcgcta | 360 |
| tgcagagaag | tactctgggg | tcttggattc | tccctacgag cgtccggccc | tgggcgggta | 420 |
| cagcgacgcc | tccttcctca | acggcgccaa | aggggatccc gagccctggc | agggccgga | 480 |
| gccaccctac | cccttggcct | cactccacga | aggcctccca ggaaccaaat | cgggcggtgg | 540 |
| cggcggttcc | ggggccctgg | ggggctcccc | agttttagcc gggaacctcc | ctgaacccct | 600 |
| ctacgccggc | aatgcgtgcg | ggggcccatc | ggcggcgccc gagtacgcgg | ccggctacgg | 660 |
| cggggggtac | ctggcgccgg | gttactgcgc | gcagacgggc gccgcgctgc | ccccgccgcc | 720 |
| cccgccgcg | ctcctgcagc | ccccaccgcc | tccggggtac gggccctcag | cgccgctgta | 780 |
| caactatccc | gcagggggct | acgcagcgca | gcccggctat ggcgcgctcc | cgccgccccc | 840 |
| aggcccaccc | ccgccccct | acctgacccc | gggcctgccc gcgcccacgc | cctgcccgc | 900 |
| gccggcaccg | cccaccgcct | atggcttccc | cacggccgcg ccgggtgccg | aatccgggct | 960 |
| gtcgctgaag | cgcaaggcg | ccgacgaggg | gcccgagggc cgctaccgca | agtacgcgta | 1020 |
| cgagcccgcc | aaggcccccg | tggctgacgg | agcctcctac cccgccgcgg | acaacggcga | 1080 |
| atgtcgggc | aacgggttcc | gggccaagc | gccaggagcc gcggaggagg | cgtcgggcaa | 1140 |
| gtacggtggc | ggcgtccccc | tcaaggtcct | gggctccccc gtctacggcc | gcaactgga | 1200 |
| gcccttgaa | aagttcccgg | agcgggcccc | ggctcctcgt gggggggttcg | ccgtgccgtc | 1260 |
| gggggagact | cccaaaggcg | tggaccctgg | ggccctggag ctggtgacga | gcaagatggt | 1320 |
| ggactgcggg | cccccggtgc | agtgggcgga | tgtggcgggc cagggcgcgc | tcaaggcggc | 1380 |
| gctggaggag | gagctggtgt | ggcccctgct | caggccgccc gcctaccgg | gcagcctgcg | 1440 |
| cccgccgcgg | accgtcctgc | tctttgggcc | gcggggcgcg ggcaaagcgc | tgctgggccg | 1500 |
| ctgcctcgcc | acgcagctgg | gcgccacgct | gttgcgcctg cgcggcgcga | ccctggctgc | 1560 |
| gcccggcgcc | gccgagggcg | cgcgcctcct | ccaggccgcc ttcgcggccg | cgcgctgccg | 1620 |
| cccaccctcc | gtactcctca | tcagcgagct | agaggcgctg ctccccgccc | gggacgacgg | 1680 |
| cgcggcggca | gggggcgcgc | tgcaggtgcc | gctcctggcc tgcctggacg | gggctgcgg | 1740 |
| cgcggggct | gacggcgtgc | tggttgtggg | caccacctcg cggcccgcgg | ctctggacga | 1800 |
| ggcgaccccgc | cggcgcttct | ctctccgctt | ctacgtggcg ctgcccgaca | gcccggcccg | 1860 |
| cgggcagatc | ctgcagcggg | cgctgggcca | gcagggctgc cgcgctcagtg | agcgggaact | 1920 |
| ggcgcgcgctg | gtgcagggca | cgcagggctt | ctctgggggc gagctggggc | agctgtgcca | 1980 |
| gcaggcggcg | gccggggcgg | gcctcccggg | gctgcagcgc cccctctcct | acaaggacct | 2040 |
| ggaggcggcg | ctggccaagg | tgggccctag | ggcctctgcc aaggaactgg | actcgttcgt | 2100 |

```
ggagtgggac aaaatgtacg gctccggaca ctgacggcgc gcgggggagg ccgcgggagc    2160
cgcagtccct ccgtccccgc cgcctccgcg tgggagggat gtcactgact aaacccggct    2220
ggcaggggct ggagtggtga atgtgggatc ggggacagga ggggtctgcc ggtggatatt    2280
ttttttttcg tgggaaggaa aatgcttctg ccaggcagat gccatatgcg ccgtgtactc    2340 aggttttcc tatttattgt ggactggaag ctcgccatct ccgcccggca gaccgggcag     2400
atccggcatg ggctggcacc cggggcctta agaactcctg ctctcttgcc acaacgcttt    2460
tgtctcctcg ctatctgaat ggcaccctcc ttctccctca ctctctccat cccattctct    2520
gcattctctt ggttttctct cccttttgct ttgtcgctga caccctgcc caccccatgc     2580 tggccctgtt tctctcctgc ccctccctcc ccagctctcc atccctcacc ctctgtgctt    2640
ctgtctccat ccctggctct ccagcgtccc tggcctttg gtccctgagc tttaatgcct     2700
ttccctgcct tctgttctta tttggactgc agtggcccct tgcaggagct ctggaggccc    2760
aggggctgag gaggagggtt accctctac ccatctgaaa cctagggtct agggggatca     2820
aggaaaaaaa gtccccaaag aaggggaatt ttttgtttgt tttgaggggg agatcccaga    2880
aatgtagctt gtttcatatt ttagtcttct tattttgta aaatgtgtag aatttgctgt     2940 ttttctttt cttttgacaa ctcaggaaga aactgacctc agaaagaatg ttagactttg     3000
gctgctctcc tgtgtgcccc tcacacctgc ccctccccc ccactccatc caggggacca    3060
aattctccca gacactcaaa aaatgagact tacggggaag gggagaggaa gacccagagg    3120
cctcagtgaa accccagcta ttcctggtca gaagcagaat gtattcctaa ggcttcctc    3180 cccagggccg aggcctaggc atgaatgtgg ggagtgggct gtggggtttg agagaaggga    3240
ggccttattc ctctcctgct gctccccacc ccctgcccca cccaacccct ccgctgagtg    3300
ttttctgtga agggctatcc agagttagga tgcccttgcc caattccttc ctgagaccca    3360
gaaggtaggg tgggagggcc caaatgggaa ggtgacctaa gcagaaagtc tccagaaagg    3420
tcatgtcccc tggccctgcc ttggcagagg tccccagtga cttatgctag gaggattcca    3480
tctgggtaga cagtctggcc acaaaatcag ctactggacc tcagccatct ctgctggagg    3540
ctctgaggag gagtgagcat ccctcacttg tggggctct gtgaggaaat gtgccttccc    3600 cattccccg gagtcctagg tctggagctc caggctggg agagggtgag ggagatgggc     3660
aggggtgttt tctctgacct tggggggctta gtctcagtcc tgcctgaact ttccactagg    3720
cttggaaccc ttccaagaac catatttctc tccttcccac caattttccc ttgatgaggc    3780
tttagcagtt tgctcccacc accccagcc catttcacaa ctctgatctt agtccaaagc     3840
aggggacacg ccccccacc accacttttt ctctctccca tctcagcctc ctgtgcagtt     3900
ccttgcctgc ccgtgcattt cctagagtct actgcctccc cctggctgg gagggtgtct    3960 gggggggatc tttcagggc cctggcaccc agggcctgtg ctggcctagg agtgctgacc     4020
agaaggctgc tctgttcccc cccacccccg ttgctttctg gccccctctt tggagccagc    4080
cacccacagg gctttggtgc ctcagaagca gtgggctgcc gggtcacagc cgcaggctgc    4140
aaaagaccct cggagggagc atggagtgag gggttctctc tcaggtgtgt atgtattggg    4200 gggtggggt ggtggaggg tgtcaggaa gttggggtgg atcccagcc ttcccttcaa        4260 gaggcaggga gctctgggag gtggagtccc caccgctttc tctactaggc tcctcctgtt    4320
ccccaggctt ggggagcttt gcacaaggag actgccccca gcctagtggc acctacctca    4380
tgggctctgg ggcaggtagg ggaagggcca gtccagctct ggtaatgctg gggggaggca    4440
```

```
taccaaagaa tccaggggca gggagtgggg agggtgactt ccgagctggc ctctcccctt    4500
cctctaccca gactggggct gggatcctct cctcccgctg taaccatttc tacctcattt    4560
tgctgcgtgt tgtacatgga cgtatttatc tcctgtctga cgatgctctg cagttgtggt    4620
ctgtctacct cagaagagac tgtattttaa aagaaagtat tacacagtat taaagcgatg    4680
acatgtggtt tgcaaaaaaa aaaaaaaaaa a                                    4711

<210> SEQ ID NO 2
<211> LENGTH: 653
<212> TYPE: PRT
<213> ORGANISM: HOMO SAPIENS

<400> SEQUENCE: 2
```

| Met | His | Trp | Thr | Pro | Glu | His | Ala | Gln | Pro | Leu | Asn | Gln | Trp | Pro | Glu |
|---|---|---|---|---|---|---|---|---|---|---|---|---|---|---|---|
| 1 | | | | 5 | | | | | 10 | | | | | 15 | |

Gln His Leu Asp Val Ser Ser Thr Thr Pro Ser Pro Ala His Lys Leu
                20                  25                  30

Glu Leu Pro Pro Gly Gly Arg Gln Arg Cys His Tyr Ala Trp Ala His
            35                  40                  45

Asp Asp Ile Ser Ala Leu Thr Ala Ser Asn Leu Leu Lys Arg Tyr Ala
 50                  55                  60

Glu Lys Tyr Ser Gly Val Leu Asp Ser Pro Tyr Glu Arg Pro Ala Leu
 65                  70                  75                  80

Gly Gly Tyr Ser Asp Ala Ser Phe Leu Asn Gly Ala Lys Gly Asp Pro
                85                  90                  95

Glu Pro Trp Pro Gly Pro Glu Pro Pro Tyr Pro Leu Ala Ser Leu His
            100                 105                 110

Glu Gly Leu Pro Gly Thr Lys Ser Gly Gly Gly Gly Ser Gly Ala
        115                 120                 125

Leu Gly Gly Ser Pro Val Leu Ala Gly Asn Leu Pro Glu Pro Leu Tyr
130                 135                 140

Ala Gly Asn Ala Cys Gly Gly Pro Ser Ala Ala Pro Glu Tyr Ala Ala
145                 150                 155                 160

Gly Tyr Gly Gly Gly Tyr Leu Ala Pro Gly Tyr Cys Ala Gln Thr Gly
                165                 170                 175

Ala Ala Leu Pro Pro Pro Pro Ala Ala Leu Leu Gln Pro Pro
            180                 185                 190

Pro Pro Gly Tyr Gly Pro Ser Ala Pro Leu Tyr Asn Tyr Pro Ala Gly
        195                 200                 205

Gly Tyr Ala Ala Gln Pro Gly Tyr Gly Ala Leu Pro Pro Pro Gly
    210                 215                 220

Pro Pro Ala Pro Tyr Leu Thr Pro Gly Leu Pro Ala Pro Thr Pro
225                 230                 235                 240

Leu Pro Ala Pro Ala Pro Thr Ala Tyr Gly Phe Pro Thr Ala Ala
                245                 250                 255

Pro Gly Ala Glu Ser Gly Leu Ser Leu Lys Arg Lys Ala Ala Asp Glu
            260                 265                 270

Gly Pro Glu Gly Arg Tyr Arg Lys Tyr Ala Tyr Glu Pro Ala Lys Ala
        275                 280                 285

Pro Val Ala Asp Gly Ala Ser Tyr Pro Ala Ala Asp Asn Gly Glu Cys
    290                 295                 300

Arg Gly Asn Gly Phe Arg Ala Lys Pro Gly Ala Ala Glu Glu Ala
305                 310                 315                 320

Ser Gly Lys Tyr Gly Gly Gly Val Pro Leu Lys Val Leu Gly Ser Pro

|     |     |     |     |     | 325 |     |     |     | 330 |     |     |     |     | 335 |
| --- | --- | --- | --- | --- | --- | --- | --- | --- | --- | --- | --- | --- | --- | --- |
| Val | Tyr | Gly | Pro | Gln | Leu | Glu | Pro | Phe | Glu | Lys | Phe | Pro | Glu | Arg | Ala |
|     |     |     | 340 |     |     |     |     | 345 |     |     |     |     | 350 |     |     |

Pro Ala Pro Arg Gly Gly Phe Ala Val Pro Ser Gly Glu Thr Pro Lys
        355                 360                 365

Gly Val Asp Pro Gly Ala Leu Glu Leu Val Thr Ser Lys Met Val Asp
370                 375                 380

Cys Gly Pro Pro Val Gln Trp Ala Asp Val Ala Gly Gln Gly Ala Leu
385                 390                 395                 400

Lys Ala Ala Leu Glu Glu Leu Val Trp Pro Leu Leu Arg Pro Pro
                405                 410                 415

Ala Tyr Pro Gly Ser Leu Arg Pro Arg Thr Val Leu Leu Phe Gly
                420                 425                 430

Pro Arg Gly Ala Gly Lys Ala Leu Leu Gly Arg Cys Leu Ala Thr Gln
                435                 440                 445

Leu Gly Ala Thr Leu Leu Arg Leu Arg Gly Ala Thr Leu Ala Ala Pro
                450                 455                 460

Gly Ala Ala Glu Gly Ala Arg Leu Leu Gln Ala Ala Phe Ala Ala Ala
465                 470                 475                 480

Arg Cys Arg Pro Pro Ser Val Leu Leu Ile Ser Glu Leu Glu Ala Leu
                485                 490                 495

Leu Pro Ala Arg Asp Asp Gly Ala Ala Ala Gly Gly Ala Leu Gln Val
                500                 505                 510

Pro Leu Leu Ala Cys Leu Asp Gly Gly Cys Gly Ala Gly Ala Asp Gly
                515                 520                 525

Val Leu Val Val Gly Thr Thr Ser Arg Pro Ala Ala Leu Asp Glu Ala
530                 535                 540

Thr Arg Arg Arg Phe Ser Leu Arg Phe Tyr Val Ala Leu Pro Asp Ser
545                 550                 555                 560

Pro Ala Arg Gly Gln Ile Leu Gln Arg Ala Leu Ala Gln Gln Gly Cys
                565                 570                 575

Ala Leu Ser Glu Arg Glu Leu Ala Ala Leu Val Gln Gly Thr Gln Gly
                580                 585                 590

Phe Ser Gly Gly Glu Leu Gly Gln Leu Cys Gln Gln Ala Ala Ala Gly
                595                 600                 605

Ala Gly Leu Pro Gly Leu Gln Arg Pro Leu Ser Tyr Lys Asp Leu Glu
                610                 615                 620

Ala Ala Leu Ala Lys Val Gly Pro Arg Ala Ser Ala Lys Glu Leu Asp
625                 630                 635                 640

Ser Phe Val Glu Trp Asp Lys Met Tyr Gly Ser Gly His
                645                 650

<210> SEQ ID NO 3
<211> LENGTH: 21
<212> TYPE: RNA
<213> ORGANISM: ARTIFICIAL SEQUENCE
<220> FEATURE:
<223> OTHER INFORMATION: STRAND OF SIRNA DIRECTED TO HUMAN
      FIDGETIN-LIKE 2

<400> SEQUENCE: 3
uuacacagua uuaaagcgau u                                              21

<210> SEQ ID NO 4
<211> LENGTH: 21
<212> TYPE: RNA

```
<213> ORGANISM: ARTIFICIAL SEQUENCE
<220> FEATURE:
<223> OTHER INFORMATION: STRAND OF SIRNA DIRECTED TO HUMAN
      FIDGETIN-LIKE 2

<400> SEQUENCE: 4
ucgcuuuaau acuguguaau u                                              21

<210> SEQ ID NO 5
<211> LENGTH: 21
<212> TYPE: RNA
<213> ORGANISM: ARTIFICIAL SEQUENCE
<220> FEATURE:
<223> OTHER INFORMATION: STRAND OF SIRNA DIRECTED TO HUMAN
      FIDGETIN-LIKE 2

<400> SEQUENCE: 5
caucugaaac cuagggucuu u                                              21

<210> SEQ ID NO 6
<211> LENGTH: 21
<212> TYPE: RNA
<213> ORGANISM: ARTIFICIAL SEQUENCE
<220> FEATURE:
<223> OTHER INFORMATION: STRAND OF SIRNA DIRECTED TO HUMAN
      FIDGETIN-LIKE 2

<400> SEQUENCE: 6
agacccuagg uuucagaugu u                                              21

<210> SEQ ID NO 7
<211> LENGTH: 21
<212> TYPE: RNA
<213> ORGANISM: ARTIFICIAL SEQUENCE
<220> FEATURE:
<223> OTHER INFORMATION: STRAND OF SIRNA DIRECTED TO HUMAN
      FIDGETIN-LIKE 2

<400> SEQUENCE: 7
gugacuuaug cuaggaggau u                                              21

<210> SEQ ID NO 8
<211> LENGTH: 21
<212> TYPE: RNA
<213> ORGANISM: ARTIFICIAL SEQUENCE
<220> FEATURE:
<223> OTHER INFORMATION: STRAND OF SIRNA DIRECTED TO HUMAN
      FIDGETIN-LIKE 2

<400> SEQUENCE: 8
uccuccuagc auaagucacu u                                              21

<210> SEQ ID NO 9
<211> LENGTH: 21
<212> TYPE: RNA
<213> ORGANISM: ARTIFICIAL SEQUENCE
<220> FEATURE:
<223> OTHER INFORMATION: STRAND OF SIRNA DIRECTED TO HUMAN
      FIDGETIN-LIKE 2

<400> SEQUENCE: 9
ggucagaagc agaauguauu u                                              21

<210> SEQ ID NO 10
<211> LENGTH: 21
<212> TYPE: RNA
<213> ORGANISM: ARTIFICIAL SEQUENCE
```

<220> FEATURE:
<223> OTHER INFORMATION: STRAND OF SIRNA DIRECTED TO HUMAN
      FIDGETIN-LIKE 2

<400> SEQUENCE: 10
auacauucug cuucugaccu u                                                  21

<210> SEQ ID NO 11
<211> LENGTH: 759
<212> TYPE: PRT
<213> ORGANISM: HOMO SAPIENS

<400> SEQUENCE: 11

Met Ile Ser Ser Thr Ser Val Tyr Gly Leu Lys Met Gln Trp Thr Pro
1               5                   10                  15

Glu His Ala Gln Trp Pro Glu Gln His Phe Asp Ile Thr Ser Thr Thr
            20                  25                  30

Arg Ser Pro Ala His Lys Val Glu Ala Tyr Arg Gly His Leu Gln Arg
        35                  40                  45

Thr Tyr Gln Tyr Ala Trp Ala Asn Asp Asp Ile Ser Ala Leu Thr Ala
    50                  55                  60

Ser Asn Leu Leu Lys Lys Tyr Ala Glu Lys Tyr Ser Gly Ile Leu Glu
65                  70                  75                  80

Gly Pro Val Asp Arg Pro Val Leu Ser Asn Tyr Ser Asp Thr Pro Ser
                85                  90                  95

Gly Leu Val Asn Gly Arg Lys Asn Glu Ser Glu Pro Trp Gln Pro Ser
            100                 105                 110

Leu Asn Ser Glu Ala Val Tyr Pro Met Asn Cys Val Pro Asp Val Ile
        115                 120                 125

Thr Ala Ser Lys Ala Gly Val Ser Ser Ala Leu Pro Pro Ala Asp Val
    130                 135                 140

Ser Ala Ser Ile Gly Ser Ser Pro Gly Val Ala Ser Asn Leu Thr Glu
145                 150                 155                 160

Pro Ser Tyr Ser Ser Ser Thr Cys Gly Ser His Thr Val Pro Ser Leu
                165                 170                 175

His Ala Gly Leu Pro Ser Gln Glu Tyr Ala Pro Gly Tyr Asn Gly Ser
            180                 185                 190

Tyr Leu His Ser Thr Tyr Ser Ser Gln Pro Ala Pro Ala Leu Pro Ser
        195                 200                 205

Pro His Pro Ser Pro Leu His Ser Ser Gly Leu Leu Gln Pro Pro Pro
    210                 215                 220

Pro Pro Pro Pro Pro Ala Leu Val Pro Gly Tyr Asn Gly Thr Ser
225                 230                 235                 240

Asn Leu Ser Ser Tyr Ser Tyr Pro Ser Ala Ser Tyr Pro Pro Gln Thr
                245                 250                 255

Ala Val Gly Ser Gly Tyr Ser Pro Gly Gly Ala Pro Pro Pro Ser
            260                 265                 270

Ala Tyr Leu Pro Ser Gly Ile Pro Ala Pro Thr Pro Leu Pro Pro Thr
        275                 280                 285

Thr Val Pro Gly Tyr Thr Tyr Gln Gly His Gly Leu Thr Pro Ile Ala
    290                 295                 300

Pro Ser Ala Leu Thr Asn Ser Ser Ala Ser Ser Leu Lys Arg Lys Ala
305                 310                 315                 320

Phe Tyr Met Ala Gly Gln Gly Asp Met Asp Ser Ser Tyr Gly Asn Tyr
                325                 330                 335

```
Ser Tyr Gly Gln Gln Arg Ser Thr Gln Ser Pro Met Tyr Arg Met Pro
            340                 345                 350

Asp Asn Ser Ile Ser Asn Thr Asn Arg Gly Asn Gly Phe Asp Arg Ser
            355                 360                 365

Ala Glu Thr Ser Ser Leu Ala Phe Lys Pro Thr Lys Gln Leu Met Ser
    370                 375                 380

Ser Glu Gln Gln Arg Lys Phe Ser Ser Gln Ser Ser Arg Ala Leu Thr
385                 390                 395                 400

Pro Pro Ser Tyr Ser Thr Ala Lys Asn Ser Leu Gly Ser Arg Ser Ser
            405                 410                 415

Glu Ser Phe Gly Lys Tyr Thr Ser Pro Val Met Ser Glu His Gly Asp
            420                 425                 430

Glu His Arg Gln Leu Leu Ser His Pro Met Gln Gly Pro Gly Leu Arg
            435                 440                 445

Ala Ala Thr Ser Ser Asn His Ser Val Asp Glu Gln Leu Lys Asn Thr
    450                 455                 460

Asp Thr His Leu Ile Asp Leu Val Thr Asn Glu Ile Ile Thr Gln Gly
465                 470                 475                 480

Pro Pro Val Asp Trp Asn Asp Ile Ala Gly Leu Asp Leu Val Lys Ala
            485                 490                 495

Val Ile Lys Glu Glu Val Leu Trp Pro Val Leu Arg Ser Asp Ala Phe
            500                 505                 510

Ser Gly Leu Thr Ala Leu Pro Arg Ser Ile Leu Leu Phe Gly Pro Arg
            515                 520                 525

Gly Thr Gly Lys Thr Leu Leu Gly Arg Cys Ile Ala Ser Gln Leu Gly
            530                 535                 540

Ala Thr Phe Phe Lys Ile Ala Gly Ser Gly Leu Val Ala Lys Trp Leu
545                 550                 555                 560

Gly Glu Ala Glu Lys Ile Ile His Ala Ser Phe Leu Val Ala Arg Cys
            565                 570                 575

Arg Gln Pro Ser Val Ile Phe Val Ser Asp Ile Asp Met Leu Leu Ser
            580                 585                 590

Ser Gln Val Asn Glu Glu His Ser Pro Val Ser Arg Met Arg Thr Glu
            595                 600                 605

Phe Leu Met Gln Leu Asp Thr Val Leu Thr Ser Ala Glu Asp Gln Ile
            610                 615                 620

Val Val Ile Cys Ala Thr Ser Lys Pro Glu Glu Ile Asp Glu Ser Leu
625                 630                 635                 640

Arg Arg Tyr Phe Met Lys Arg Leu Leu Ile Pro Leu Pro Asp Ser Thr
            645                 650                 655

Ala Arg His Gln Ile Ile Val Gln Leu Leu Ser Gln His Asn Tyr Cys
            660                 665                 670

Leu Asn Asp Lys Glu Phe Ala Leu Leu Val Gln Arg Thr Glu Gly Phe
            675                 680                 685

Ser Gly Leu Asp Val Ala His Leu Cys Gln Glu Ala Val Val Gly Pro
            690                 695                 700

Leu His Ala Met Pro Ala Thr Asp Leu Ser Ala Ile Met Pro Ser Gln
705                 710                 715                 720

Leu Arg Pro Val Thr Tyr Gln Asp Phe Glu Asn Ala Phe Cys Lys Ile
            725                 730                 735

Gln Pro Ser Ile Ser Gln Lys Glu Leu Asp Met Tyr Val Glu Trp Asn
            740                 745                 750

Lys Met Phe Gly Cys Ser Gln
```

<210> SEQ ID NO 12
<211> LENGTH: 4535
<212> TYPE: DNA
<213> ORGANISM: HOMO SAPIENS

<400> SEQUENCE: 12

```
gggtttgaaa ttccaacatg gcagaggctg cagtccgtct tcccttcaaa aacttggaat      60
gatttcaaat cataggcacc ttcacttaac cctagcttcc attcatcagc aaacacatcg     120
gatcgatgct acgctaacct atcgggttct ctctccgcgc gttcaggtta aatgaatacc     180
tgacgaaagg gcccacgttt caaggcagtg acatttgata gctgagagga aaagtggctt     240
taatgaaaag caacctttgg aattcctgct tgtgagaaat ccaattcagc ttttgtgct      300
gccagcaaga aatgatcagt agcaccagtg tttatggctt gaagatgcag tggacgccag     360
agcatgccca gtggccagaa cagcactttg acatcacctc aaccactcgg tctcctgccc     420
acaaagttga agcctacaga ggtcatctgc agcgcaccta tcagtacgcc tgggcgaatg     480
atgacatatc tgctctgact gcatccaacc tactaaaaaa atatgcagag aagtattccg     540
gcattttgga aggtcctgtg gaccgacccg tactcagcaa ctattcggac acaccatcag     600
gactagtgaa cggtcggaaa aatgaaagtg aaccctggca gccttccttg aattcagaag     660
ctgtttatcc catgaactgt gttccggatg ttatcactgc cagcaaagct ggagtcagtt     720
cagccctccc tccagcagat gtctctgcga gtataggaag ctctcctggg gtagccagca     780
acctgacaga acctagttat tcaagtagta cctgtggaag ccacactgta cccagtcttc     840
atgcagggct cccatctcag gaatatgccc caggatacaa cggatcatat ttgcattcta     900
cttatagtag ccagccagca cctgcacttc cttcacctca tccgtctcct ttgcatagct     960
ctgggctact acagccccca ccaccacctc ctccgccacc agccttggtc ccaggctaca    1020
atgggacttc taacctctcc agttacagct atccgtctgc tagctatcct cctcagactg    1080
ctgtggggtc tgggtacagc cctggggggg caccgcctcc gccttcagcg tacctgcctt    1140
caggaattcc tgctcccacc cccctacccc ccaccactgt tcctggctac acctaccagg    1200
gccatggttt gacacctatt gcaccgtcgg ctctgacaaa cagttcagca agttctctca    1260
aaaggaaagc tttctacatg gcagggcaag gagatatgga ctccagttat ggaaattaca    1320
gctatggcca acagagatct acacagagtc ctatgtacag aatgcccgac aacagcattt    1380
caaacacaaa tcgggggaat ggcttttgaca gaagtgctga acatcatcc ttagcattta    1440
agccaacgaa gcagctaatg tcctctgaac agcaaaggaa attcagcagc cagtccagta    1500
gggctctgac ccctccttcc tacagtactg ctaaaaattc attgggatca agatccagtg    1560
aatcctttgg gaagtacaca tcgccagtaa tgagtgagca tggggacgag cacaggcagc    1620
tcctctctca cccaatgcaa ggccctggac tccgtgcagc tacctcatcc aaccactctg    1680
tggacgagca actgaagaat actgacacgc acctcatcga cctggtaacc aatgagatta    1740
tcacccaagg acctccagtg gactggaatg acattgctgg tctcgacctg gtgaaggctg    1800
tcattaaaga ggaggtttta tggccagtgt tgaggtcaga cgcgttcagt ggactgacgg    1860
ccttacctcg gagcatcctt ttatttggac ctcgggggac aggcaaaaca ttattgggca    1920
gatgcatcgc tagtcagctg ggggccacat tttcaaaat tgccggttct ggactagtcg    1980
ccaagtggtt aggagaagca gagaaaatta tccatgcctc ttttcttgtg ccaggtgtc    2040
gccagccctc ggtgattttt gttagtgaca ttgacatgct tctctcctct caagtgaatg    2100
```

```
aggaacatag tccagtcagt cggatgagaa ccgaatttct gatgcaactg gacactgtac    2160
taacttcggc tgaggaccaa atcgtagtaa tttgtgccac cagtaaacca gaagaaatag    2220
atgaatccct tcggaggtac ttcatgaaac gacttttaat cccacttcct gacagcacag    2280
cgaggcacca gataatagta caactgctct cacagcacaa ttactgtctc aatgacaagg    2340
agtttgcact gctcgtccag cgcacagaag gcttttctgg actagatgtg gctcatttgt    2400
gtcaggaagc agtggtgggc cccctccatg ccatgccagc cacagacctt tcagccatta    2460
tgcccagcca gttgaggccc gttacatatc aagactttga aaatgctttc tgcaagattc    2520
agcctagcat atctcaaaag gagcttgata tgtatgttga atggaacaaa atgtttggtt    2580
gcagtcagtg ataacttctt tagaaaaaaa aaatgtaatg aatgttggca cacacacata    2640
aaacctgcta cataggggaat agagccccctt tccagtagag tttaaattgc aaagggtact    2700
ggggaagatg acgattaagt tgcatcttta gagtcagggt agatttggag gaaaagtgca    2760
tcaaatgaga gcttctgatt tgaaagcccc agatgacaga aagcatatgt ggatgctcag    2820
ttctgttcaa gctagacaac actcaccaag gagcaaggtg caagtgtgtt gatttcagaa    2880
ggacatgaac ctcgtgtgtt gattccattc tgctgttctc gagatttagt tgctgtcaag    2940
tgcctggagt ggtgctttat tttttgtttg cctcacaatt acattggtgg catgtgctaa    3000
tataaagagc tttaacttca aacattattg gactaaagag atgaacagtt gtgttatgac    3060
agaaaaccag attttgcca ttttaagagc aacagtattc ctcaatcctg tctgttctgc    3120
agtattaagc taagaacagg taaaacaggg taacggtaat ctggacctta atttctgcag    3180
ttcatttctt ttaatgttct tgtctgcaaa aactcaggaa agtgattgtg atttgtacag    3240
tacctcaaag gaatgtgttg aaagcactat gtactgctga gagtaatagg ataggcttca    3300
atgttacttt atattaaaat gtatgtttac ctcaacaatt ggaaaatagc aaggaaaatt    3360
actttgaatg tatccagaaa aatactgaag tgtgatacaa ctgaatattt acagtttaaa    3420
gtagaaatgg aaggattttt ttaagttctt ttactaatta tggggaatta accagagcag    3480
aataattctt tatgtcaata actgcaagag ttcttagtac attgctcctt gataattaag    3540
tgaaaatgtt cttaaaaggt acactggtta attgaaagct acttattcag tttgtgttag    3600
tgtctagacc tgtcagccac aagacctgtt taggaccctg aaagtcacag tacctaaaaa    3660
ctatgactgc cttttattg cataggtggt agtggtggtg atggtggtgg tagtttgcaa    3720
gttatctctt aaaactgctg ggaatggtgt cattctattc actaatctag cttatagact    3780
tgccgtgctg tttgatagaa tgcagaggat agcaaccaaa acaaatacac aaataaataa    3840
aaacaaaaac caaccaacaa accaacttac atacacatat atatatccac aaagaacctc    3900
tccatctcct ccccttcttt ttgactccac tcttgtcagt gcaattttgc ttctcatttt    3960
gaaatctggg ctgtagtgct cctgctttat ttctacctca gttttgttac atttctcttg    4020
gaaagtaaag tagaaaattg gaagtggaca cacacactgc aatgtagctt gccaaacatg    4080
ttactttgtt ttcttccatc tttcaccgta aatctagttt ccaaagacat cagcatttgt    4140
gcttacttcc acctcagtct accagcccca cccctaccca tggcataagt ggcatttttc    4200
ttaatttcct attttttctcc tgctctctgt caagttgttc tttgtatcct ttaatgcttt    4260
atgtgcaacc tttcattgat agtgggctga tgtttggcaa tgcttctgaa ctgtcacaga    4320
gcaggctgta gctttccaca gccactgccc atgcataagc agaacagcct ggccttttga    4380
atgtattttc ctgggttttt tcccctttc tttttttagt ttagagatgc agtaacaaaa    4440
```

```
ctgttgcaaa gcactggcat tttatgtatt caataaataa gtgatgtaca tttttaaaaa    4500
aatttaaata aatgcaatga gaagccccaa gaaag                               4535
```